United States Patent
Ogata et al.

(10) Patent No.: US 7,601,828 B2
(45) Date of Patent: Oct. 13, 2009

(54) ESTIMATION METHOD, HUMAN ESTROGEN RECEPTOR ALPHA GENE, GENOMIC DNA, AND DIAGNOSTIC MARKER

(75) Inventors: Tsutomu Ogata, Tokyo (JP); Naoyuki Kamatani, Tokyo (JP); Tomonobu Hasegawa, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 11/434,940

(22) Filed: May 16, 2006

(65) Prior Publication Data

US 2007/0269809 A1    Nov. 22, 2007

(51) Int. Cl.
*C12N 15/12* (2006.01)
*C12Q 1/68* (2006.01)

(52) U.S. Cl. .................. 536/23.5; 536/23.1; 536/24.31; 435/6

(58) Field of Classification Search ........................ None
See application file for complete search history.

(56) References Cited

U.S. PATENT DOCUMENTS

2001/0053519 A1* 12/2001 Fodor et al. .................. 435/6

OTHER PUBLICATIONS

Moller, et al. Neuroscience Letters, Apr. 15, 2004; 359(3): 195-197.*
NCBI dbSNP Accession No. rs6932902, assay ID# ss10332135, entry date Jun. 29, 2003, URL: http://www.ncbi.nlm.nih.gov/SNP/snp_ref.cgi. ?rs=6932902.*
Yoshida, R. et al. (2005) Association of Cryptorchidism with a Specific Haplotype of the Estrogen Receptor α Gene: Implication for the Susceptibility to Estrogenic Environmental Endocrine Disruptors, *J. Clinical of Endocrinology & Metabolism*, 90(8):4716-4721.
Ito, T. et al. (2004) Association Test Algorithm Between a Qualitative Phenotype and a Haplotype or Haplotype Set Using Simultaneous Estimation of Haplotype Frequencies, Diplotype Configurations and Diplotype-Based Penetrances, *Genetics*, 168(4):2339-2348.
Kamatani, N. et al. (2004) Large-Scale Single-Nucleotide Polymorphism (SNP) and Haplotype Analyses, Using Dense SNP Maps, of 1999 Drug-Related Genes in 752 Subjects: the Analysis of the Association between Uncommon SNPs within Haplotype Blocks and the Haplotypes Constructed with Haplotype-Tagging SNPs, *Am. J. Hum. Genet.* 75(2):190-203.
Zhu, X. et al. (2003) Linkage Disequilibrium and Haplotype Diversity in the Genes of the Renin-Angiotensin System: Findings From the Family Blood Pressure Program, *Genome Research*, 13(2):173-181.
Kawaguchi, Y. et al. (2003) Association of *IL1A* Gene Polymorphisms with Susceptibility to and Severity of Systemic Sclerosis in the Japanese Population, *Arthritis & Rheumatism*, 48(1):186-192.

* cited by examiner

*Primary Examiner*—James Martinell
(74) *Attorney, Agent, or Firm*—Tarolli, Sundheim, Covell & Tummino LLP

(57) ABSTRACT

Evaluation methods for evaluating susceptibility to multifactorial diseases in sexual differentiation disorders, human estrogen receptor alpha (α) genes carrying single nucleotide polymorphisms (SNPs) associated with the multifactorial diseases, DNAs containing the nucleotides at the SNPs, and diagnostic markers containing the DNAs are provided. Susceptibility to the multifactorial diseases can be evaluated by examining at least one of SNPs 8 to 14, or SNPs 10 to 14, in a human estrogen receptor α gene, and more precisely evaluated by examining a diplotype encompassing SNPs 10 to 14.

2 Claims, 2 Drawing Sheets

(1) Nucleotide sequence around SNP8 (SEQ ID NO.1)
AATTTTTTCTCAAATGAATTCAGTTTTTTGTTTTTTTCTTACCACTGGTTTTTACTGCA
TAGCGTTTGCCTGAAGAACACCACTTTGTTTCCCAAGGCAGTAGTCACTACAAGGC[G/A]
(SNP8)AGTTTTGTTCTGTCTATCCCAAGGCAAATAGACAGCAGCAAACATAGTGTGGAG
GGCTGCTGGGTTCAGTAGAAAACCATCAACTATTTCTA
(2) Nucleotide sequence around SNP9 (SEQ ID NO.2)
CGGTGAAGCTTCAGAGAACTTTATTAGGTATGTTTACTTAACAAAAGAGTGCATTGGGGG
TGATGAAGCCTAGTCAAATTCACAGAAAGCTAAG[G/A](SNP9)ATAACTTTCTGCTAG
ACATTACCTCAGAAGAATTCTATTATTTCTAATACACACACACACACACACACACACACA
CACTCACACTCTCTCTCTCTCTCTCTGTCATTATGAAT
(3) Nucleotide sequence around SNP10 (SEQ ID NO.3)
TGGGCTACAGTTTCATCTGCTTTGTGGACAGAAGTGCCACAAAGAGCCGAATTGTCAGTG
CAGACCCACATGAATCATAGATCTTAACGA[G/A](SNP10)GTTTTTACTAACGACTAG
CAAAGGATACAAGCTAAAAATGGGTACAAGCAAACACAGCATCATTCATCACTGTAAAGA
CTCTGAACTATCACATGGAACTTCAAAAGGATTCTTCTTCT
(4) Nucleotide sequence around SNP11 (SEQ ID NO.4)
TCTGCATTTGAATGATCATTTGGGAGACTCTTATTGTCCTATTTGCACTGAAAAAGTCAC
TGAATCATTATTTTAGAACTGGAATAAC[G/A](SNP11)CCTGAGATCTAGGCCAGCAC
TTTGCAAGTTGTGCTCTATGGGACTTTTCATGGAAGTGGCTGAGGAGTTGCCTTGAAGGA
AGGCAGAGGGAGTGGGTCTTGGGACACCCTTCCAGTTATAA
(5) Nucleotide sequence around SNP12 (SEQ ID NO.5)
CCAGGGTTCACTTTTCCTCATGTCCTCGCCGACAAGCCTGATATTCTTATTTGCCTCTTA
GCGCTTCAGCCTTTCCCTC[G/A](SNP12)TGACTTAACGGTGACTCCCTTGAGACTAC
TTGAAATAATAAGTTTGGATGGCAAGGAAATACCCTTCTGCTGTCACCCTTTGCCATAAG
ACTGAGTTACTTTGTAAACAAAGAAGATTTACTTGGTCTTC
(6) Nucleotide sequence around SNP13 (SEQ ID NO.6)
GGGTCCAGATCCCACAATGGCTCTTTATTGGATGAGAGTTCTGGGAGCAGTGCCACTCAG
CTACATGGTGCCAGGTCCTGAACCTGTGCCTTCTT[C/T](SNP13)GGTGGAGGGCTGG
CACGTGCTGACAGCTTTCATGTGGGCAATCTGGGAACTTCAGAGAAGGCAGGCCTATTAA
GTGTTAAGACTCCCCACCCCGAACTTTTACTGAGAAAAAGT
(7) Nucleotide sequence around SNP14 (SEQ ID NO.7)
CAATTGAATTTCCACTAAAATAAAATAGCTCTCTAGTATATTACAAAACTACCCATTCTG
CAAACTGCAGGGGAGCTACTGAT[C/A](SNP14)ATGCTTGGAACTGTGCCAGGCACTG
CCTGCATAAAAATGAGTAAGGTCCACTTCCTCCATGGACTGGGTTGGGTAGGAGGCAAAG
ATAATTAACCAATTATTTTAATATTATGAGTTCAGGGTTGT

Fig.1

ESTIMATION METHOD, HUMAN ESTROGEN RECEPTOR ALPHA GENE, GENOMIC DNA, AND DIAGNOSTIC MARKER

BACKGROUND OF THE INVENTION

1. Field of the Invention

The present invention relates to evaluation methods for evaluating susceptibility to multifactorial diseases in sexual differentiation disorders, a human estrogen receptor alpha ($\alpha$) gene carrying single nucleotide polymorphisms (hereafter abbreviated as SNPs) associated with the multifactorial diseases, DNAs containing nucleotides at the SNPs, and diagnostic markers composed of the DNAs.

2. Description of the Related Art

Sexual differentiation proceeds under the temporally and spatially strict control based on the heredity program that specifies the expression of the sexual phenotype of a person, resulting in occurrence of sexual phenotypes, such as gonad formation, formation of sexual ducts and external genitalia, appearance of the secondary sex characteristics, and gametogenesis. This sexual differentiation process is characterized by the followings:

(1) In gonad formation and external genitalia differentiation, precursors common to both sexes are formed during early developmental stages and then these precursors differentiate into different gonads and external genitalia according to the genetic sex.

(2) In sexual duct formation, organs of both sexes are formed in early developmental stages, and then only sexual ducts that match the genetic sex grow.

(3) Reproductive cells, the only cells passed on to the next generation, develop.

When a problem occurs somewhere in the proceeding process of this hereditary program, a sex differentiation disorder develops.

Among sex differentiation disorders, clinically, abnormalities of the external genitalia are common in boys. Many genes involved in abnormalities of the external genitalia in boys have been identified through gene analyses in human patients and studies with laboratory animals.

Abnormalities in these genes induce diseases of the external genitalia via either of hypoplasia of fetal testes (broadly divided into undifferentiated gonadal dysplasia and disorders of fetal testis differentiation), disorders of androgen production (broadly divided into disorders of cholesterol biosynthesis and disorders of steroid hormone synthetase), impaired androgen effect, or hypoplasia of the precursor of the external genitalia.

However, these diseases include multifactorial diseases which are not inherited in a Mendelian fashion and whose onset is suggested to be influenced not only by hereditary factors but also environmental factors. Typical examples of such diseases include micropenis, cryptorchidism, hypospadias, etc. In addition, defective spermatogenesis is considered to be caused by endocrine disruptors.

Additionally, when those females/girls carrying the same polymorphisms as above have multifactorial diseases (for example, premature thelarche, pubertas praecox, and endometriosis) ascribed to endocrine disruptors, their susceptibility to endocrine disruptors are considered to have increased.

SUMMARY OF THE INVENTION

Such disorders of the external genitalia associated with endocrine disruptors are mainly caused by fetal exposure to endocrine disruptors through the mother's body, not by the abnormality of the endocrine system etc. of the patient himself/herself. Therefore, to identify the causes of such multifactorial diseases, it is desirable to elucidate the details of the hereditary factors involved in the multifactorial disease in question. By doing so, it is possible to develop strategies on how to prevent or treat a particular disease for patients with the genetic factor for the disease.

Thus, the object of the present invention is to provide evaluation methods for evaluating susceptibility to multifactorial diseases in sexual differentiation disorders, human estrogen receptor $\alpha$ genes carrying single nucleotide polymorphisms associated with multifactorial disease, DNAs containing nucleotides at the SNPs, and diagnostic markers composed of the DNAs.

In the evaluation method according to the present invention, which evaluates susceptibility of a human individual to a multifactorial disease, among the single nucleotide polymorphisms (SNPs) in a human estrogen receptor alpha ($\alpha$) gene, a nucleotide of at least one of SNPs 8 to 14 is determined. Alternatively, at least one of SNPs 10 to 14 in the human estrogen receptor $\alpha$ gene may be determined. A haplotype encompassing SNPs 10 to 14 may also be determined. The multifactorial disease may be a multifactorial disease caused by an endocrine disrupting chemical. Alternatively, the multifactorial disease may be micropenis, cryptorchidism, and hypospadias.

In the human estrogen receptor $\alpha$ gene according to the present invention, amongthesinglenucleotidepolymorphisms (SNPs) present in the human estrogen receptor $\alpha$ gene, SNPs 8 to 14 constitute an AAAGATA haplotype. Alternatively, the SNPs 10 to 14 present in the human estrogen receptor $\alpha$ gene may constitute an AGATA haplotype.

The genomic DNA according to the present invention contains a part or a whole of the estrogen receptor gene carrying at least one of single nucleotide polymorphisms (SNPs) 8 to 14 of the human estrogen receptor $\alpha$ gene, and the at least one SNP is a high susceptibility allele. Alternatively, the genomic DNA according to the present invention may contain a part or a whole of an estrogen receptor $\alpha$ gene carrying at least one of SNPs 10 to 14 of the human estrogen receptor $\alpha$ gene, and the at least one SNP is a high susceptibility allele. Further alternatively, the genomic DNA according to the present invention may contain a part or a whole of an estrogen receptor $\alpha$ gene carrying at least one of SNPs 10, 11, 13 and 14 of the human estrogen receptor $\alpha$ gene, and the at least one SNP is a high susceptibility allele and the SNP 12 is A.

The diagnostic marker according to the present invention is a diagnostic marker for susceptibility to micropenis, cryptorchidism or hypospadias; and contains one of the abovementioned genomic DNAs.

The "multifactorial disease," as used herein, refers to a disease that is not inherited in a Mendelian fashion and whose onset is suggested to be influenced not only by a hereditary factor but also an environmental factor.

In addition, the "diagnostic marker," as used herein, refers to a marker by which a specific disease is generally diagnosed. Specifically, it refers to a gene-related substance for detecting SNPs. Examples of the diagnostic marker include a gene itself; hnRNA and mRNA, which are transcripts; a peptide, which is a translation product; and a protein, which is the end product of the gene expression; etc.

According to the present invention, evaluation methods for evaluating susceptibility to multifactorial diseases in sexual differentiation disorders, human estrogen receptor α genes carrying SNPs associated with the multifactorial diseases, DNAs containing nucleotides at the SNPs, and diagnostic markers containing the DNA can be provided.

BRIEF DESCRIPTION OF THE DRAWINGS

FIG. 1 shows the nucleotide sequences around SNPs 8 to 12 in a human estrogen receptor α gene.

DETAILED DESCRIPTION OF THE PREFERRED EMBODIMENTS

Figure 2:
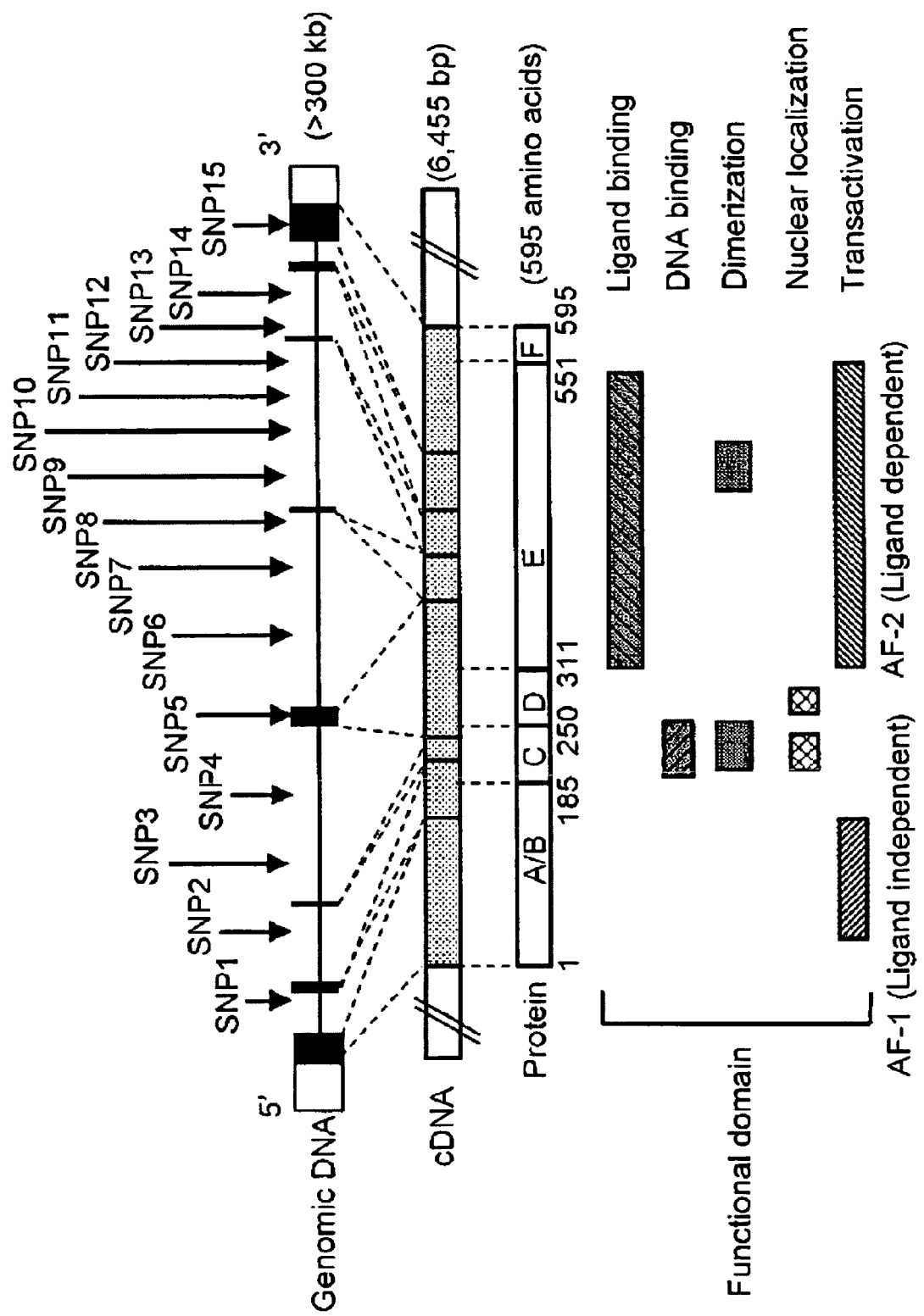
FIG. 2 shows the organization of a human estrogen receptor α gene and the positions of the SNPs in it.

Embodiments of the present invention accomplished based on the above-described findings are hereinafter described in detail by giving Examples. Unless otherwise explained, methods described in standard sets of protocols such as J. Sambrook and E. F. Fritsch & T. Maniatis (Ed.),"Molecular Cloning, a Laboratory Manual (3rd edition), Cold Spring Harbor Press and Cold Spring Harbor, N.Y. (2001); and F. M. Ausubel, R. Brent, R. E. Kingston, D. D. Moore, J. G. Seidman, J. A. Smith, and K. Struhl (Ed.) ,"Current Protocols in Molecular Biology," John Wiley & Sons Ltd., or alternatively, modified/changed methods from these are used. When using commercial reagent kits and measuring apparatus, unless otherwise explained, attached protocols to them are used.

The objective, characteristics, and advantages of the present invention as well as the idea thereof will be apparent to those skilled in the art from the descriptions given herein. It is to be understood that the embodiments and specific examples of the invention described hereinbelow are to be taken as preferred examples of the present invention. These descriptions are for illustrative and explanatory purposes only and are not intended to restrict the invention to these embodiments or examples. It is further apparent to those skilled in the art that various changes and modifications may be made based on the descriptions given herein within the intent and scope of the present invention disclosed herein.

SNPs in a Human Estrogen Receptor α Gene

FIG. 1 shows the organization of a human estrogen receptor α gene. In the human estrogen receptor α gene spanning more than 300 kb, 15 SNPs have been identified, among which SNPs 8 to 14, SNPs 10 to 14, or SNP 12 is the SNP relevant to the present invention.

FIG. 2 shows the nucleotide sequences (corresponding to SEQ ID Nos: 1 to 7) around SNPs 8 to 14.

In the human estrogen receptor cc gene according to the present invention, at least one SNP out of the nucleotides at SNP 8 (G/A) (ABI code hCV328969), SNP 9 (G/A) (ABI code hCV1141630), SNP 10 (G/A) (ABI code hCV8790212), SNP 11 (A/G) (NCBI code rs3020364), SNP 12 (G/A) (ABI code hCV2823640), SNP 13 (C/T) (ABI code hCV2823662), and SNP 14 (C/A) (NCBI code rs3020375) is a high susceptibility allele; at least one SNP out of the nucleotides at SNP 10 (G/A) (ABI code hCV8790212), SNP 11 (A/G) (NCBI code rs3020364), SNP 12 (G/A) (ABI code hCV2823640), SNP 13 (C/T) (ABI code hCV2823662), and SNP 14 (C/A) (NCBI code rs3020375) is a high susceptibility allele; or SNP 12 is A and at least one nucleotide out of the SNP 10 (G/A) (ABI code hCV8790212), SNP 11 (A/G) (NCBI code rs3020364), SNP 13 (C/T) (ABI code hCV2823662) and SNP 14 (C/A) (NCBI code rs3020375) is a high susceptibility allele. Here, the nucleotides following each SNP number are indicated as (major allele/minor allele). As described in the following Examples, the applicants have revealed that a human individual with the minor allele has a high susceptibility to a multifactorial disease. Therefore the minor allele is herein referred to as a "high susceptibility allele". It should be noted that all of these SNPs 8 to 14 are present in the introns of the human estrogen receptor a gene. Each number in parentheses indicates the database registration number.

Endocrine Disruptors and Multifactorial Diseases Aimed at by the Present Invention Among those environmental factors affecting multifactorial diseases, endocrine disruptors have recently been attracting significant attention. Endocrine disruptors are the "exogenous substances that interfere with the normal function of hormones which are intrinsically exerted in a body of an animal when taken into the body ("Strategic Programs on Environmental Endocrine Disruptors [SPEED] '98"). They are also called "environmental hormones" because of their nature. Many endocrine disrupting chemicals act like female sex hormones. For example, some endocrine disrupting chemicals, such as PCB, DDT and nonyl phenol, and bisphenol A, bind to estrogen receptors, thereby enhancing function of estrogen (estrogenic effects) . Other endocrine disrupting chemicals, such as DDE (metabolic by-product of DDT) and vincrozolin, bind to androgen (i.e., male sex hormone) receptors, thereby inhibiting the function of androgen (antiandrogenic effects).

In accordance with the present invention, when susceptibility of a human individual to multifactorial diseases is evaluated, the aforementioned SNPs in the introns of a human estrogen receptor α gene are used. Being present in the introns, these SNPs cause no changes to the primary structure of the human estrogen receptor itself. It is therefore considered that an increase in susceptibility to multifactorial diseases due to a high susceptibility allele in these SNPs does not result from an activation of the receptor molecule; rather, the high susceptibility allele is disturbing the expression of an estrogen receptor quantitatively, temporally, or locally, leading to overall enhancement of receptor activity.

Under the above-mentioned condition, an endocrine disrupting chemical with estrogenic effect delivered into the body probably expresses estrogenic effect more strongly than usual. Also, an endocrine disrupting chemical with anti-androgenic effect delivered into the body probably expresses anti-androgenic effect more strongly because, in the body, the estrogen receptor activity has been enhanced and the sex hormonal balance has been disturbed. Thus, the endocrine disrupting chemical aimed at by the present invention is not limited to any specific one as long as it generally mimic a sex hormone as an "environmental hormone," and it may have an estrogenic effect or an antiandrogenic effect. Accordingly, the disease aimed at by the present invention is not particularly limited to any specific one as long as it is a multifactorial disease ascribed to the above-mentioned endocrine disrupting chemicals.

It should be noted that, as will be shown in the Examples, degrees of its contribution to the development of symptoms differ among micropenis, cryptorchidism, and hypospadias.

The hypospadias has its highest contribution, suggesting that it is the most susceptible phenotype to the estrogenic activity by an endocrine disrupter.

Use of Diagnostic Markers

The diagnostic marker for evaluating susceptibility of a human individual to a multifactorial disease is a gene-related substance for detecting the aforementioned SNPs. Examples of the diagnostic marker include DNA containing the estrogen receptor α gene; hnRNA and mRNA, which are transcripts; a peptide, which is a translation product; a protein, which is the end product of a gene expression; etc.

When a diagnostic marker is DNA carrying an estrogen receptor a gene etc., the nucleotides at the SNPs may be directly determined to detect the aforementioned SNPs. Specifically, the nucleotide sequence may be directly determined, or various SNP typing methods such as RFLPs may be used, and the method for the detection is not particularly limited. When the diagnostic marker is hnRNA that is a transcript of an estrogen receptor α gene, SNPs can be detected by determining the RNA sequence. When the aforementioned SNPs are directly detected, the nucleic acid such as DNA or hnRNA is not required to contain an estrogen receptor α gene as a whole; it is sufficient if the nucleic acid contains a nucleotide that conytains the SNP and can be determined.

When hnRNA, mRNA, a peptide, a protein, etc. is used as the diagnostic marker, abnormalities in the expression associated with the SNP may be detected to detect the above-mentioned SNPs. Specifically, detection may be performed by, without limitation, Northern blotting, Western blotting, in situ hybridization, immunohistological methods, in situ RT-PCR, etc.

Determination of SNPs

When a nucleotide at a SNP is directly determined using the diagnostic marker for evaluating susceptibility of a human individual to a multifactorial disease, the susceptibility is judged as follows: To micropenis, cryptorchidism, or hypospadias, the individual has a high susceptibility if homozygous for one or more of the following: A at SNP 8, A at SNP 9, A at SNP 10, G at SNP11, A at SNP 12, T at SNP 13, and /A at SNP 14. Preferably, to cryptorchidism or hypospadias, an individual is judged to have a high susceptibility if homozygous for one or more of the following: A at SNP 10, G at SNP 11, A at SNP12, T at SNP 13, A at SNP 14. Also, to micropenis, cryptorchidism, or hypospadias, an individual is judged to have a high susceptibility if homozygous for A at SNP 12 as well as homozygous for one or more of the following: A at SNP 10, G at SNP 11, T at SNP 13, and A at SNP 14. As for other multifactorial diseases in sex differentiation disorders, an individual is judged to have a high susceptibility to the disease if a SNP occurring at the position characteristic to the disease is detected, in homozygosity for recessive mutation, and in heterozygosity for dominant mutation.

When expression of the diagnostic marker is detected for evaluation of susceptibility of a human individual to a multifactorial disease, the individual is judged to have a high susceptibility to the disease if any abnormal expression, in terms of expression level, expression period, or expression location, characteristic to each disease in sex differentiation disorders, is detected.

Use of Haplotypes

Linkage disequilibrium often occurs between multiple loci included in a haplotype; in evaluation of susceptibility of an individual to a multifactorial disease, taking linkage disequilibrium into consideration, it was considered preferable that the nucleotides are high susceptibility alleles at two or more consecutive SNP positions.

Thus, the haplotype block encompassing SNPs in a human estrogen receptor α gene was analyzed. Haplotypes were inferred by the software program LDSUPPORT (Kitamura et al. Ann Hum Genet 2004;75:190-203) using the maximum likelihood method. The association with the qualitative phenotype on the basis of the haplotypes was tested by PENHAPLO (Ito T. et al. Genetics 2004;168:2339-2348), which also uses the maximum likelihood method.

From this haplotype analysis, a haplotype block was identified as an approximately 50 kb region encompassing SNPs 10 to 14. Between SNPs within this block, the D' value, an indicator of strength of linkage disequilibrium, was mostly 0.9 or higher. The four haplotypes (GAGCC, AGATA, GGGTA, and AGGTA) occurring within this block counted for over 90% of all the haplotypes. Thus, using the information on the five SNP loci constituting this block, haplotype inference was practically performed in a group of cryptorchidism patients and a control group. The haplotypes involving SNPs 10 to 14 were indicated as the list of alleles at each locus (the nucleotide A, T, C, or G). A significant difference was found in the frequency of the haplotype AGATA between the two groups (34.0% in the cryptorchidism patient group vs. 22.6% in the normal group; P<0.034, as a result of a comparison of the haplotype frequency). That is, the AGATA haplotype was detected at a higher frequency in the patient group than in the normal group.

Next, diplotypes were analyzed. An individual homozygous for the AGATA haplotype can easily be detected from the genotype information of these loci. The frequency of homozygotes for this haplotype was markedly different between the two groups (15.9% in the cryptorchidism patient group vs. 2.4% in the normal group; P<0.0040). By performing the PENHAPLO algorithm to test the association between the diplotypes and phenotypes, a marked correlation (P<0.0029) was found in the recessive model (comparison between subjects carrying two identical haplotypes and the other subjects).

These findings indicate that, in evaluation of susceptibility of an individual to a multifactorial disease, an individual can be judged to have a high susceptibility to the multifactorial disease with more accuracy if AGATA is detected in a haplotype, preferably in a diplotype.

Further, when susceptibility is evaluated on the basis of one SNP, it is preferable to determine the SNP 12 because the four haplotypes account for 90% and that the A allele occurs only in the haplotype highly associated with the patient, and a high susceptibility to a multifactorial disease can be judged particularly accurately as well as quickly and easily if the SNP 12 is homozygous for the A allele.

Similarly, haplotype inference was performed in a group of micropenis patients and a control group. As a result, for SNPs 8 to 14, the frequency of the AAAGATA haplotype was significantly higher in the group of micropenis patients, indicating a weak haplotype block encompassing SNPs 8 to 14; thus the AAAGATA haplotype may be used for the methods for evaluating susceptibility to a multifactorial disease.

Also similarly, haplotype inference was performed in a group of hypospadias patients and a control group. As a result, for SNPs 10 to 14, the frequency of the AGATA haplotype was significantly higher in the group of hypospadias patients (41.9% in the hypospadias patient group vs. 22.6% in the normal group; P<0.0024, odds ratio=2.46; as a result of a comparison of the haplotype frequency). Further, diplotype analysis was also performed. As a result, the frequency of homozygotes for the AGATA haplotype was significantly higher in the group of hypospadias patients (25.6% in the hypospadias patient group vs. 2.4% in the normal group, P<0.000057, odds ratio=13.75).

These findings indicate that, in evaluation of susceptibility to hypospadias, it can be determined that an individual has a high susceptibility to hypospadias, if AGATA is detected in a haplotype, preferably in a diplotype. When the susceptibility is evaluated on the basis of one SNP, it is preferable to determine the SNP 12 because the A allele of SNP 12 occurs only in the haplotype highly associated with the patient, and a high susceptibility to hypospadias can be judged particularly accurately as well as quickly and easily if the SNP 12 is homozygous for the A allele.

Taken together, it was demonstrated that there is a linkage disequilibrium encompassing the SNPs 8 to 14 in an human estrogen receptor α gene, and a stronger linkage disequilibrium encompassing SNPs 10 to 14. Therefore, susceptibility to a multifactorial disease can be evaluated by using SNPs 8 to 14, and more preferably SNPs 10 to 14.

Method for Utilizing SNP Determination

Individuals who have been judged to have a high susceptibility to a multifactorial disease in sex differentiation disorders as described above is considered to have a high susceptibility to endocrine disrupters. Thus, an endocrine disrupter triggers the onset of a multifactorial disease at a lower concentration in such individuals than in normal individuals.

However, a multifactorial disease such as micropenis, cryptorchidism, or hypospadias develops in a boy due to the influence of endocrine disruptors to which his mother was exposed during his fetal period. Therefore, when the fetus is judged to have a high susceptibility to a multifactorial disease from the polymorphisms in his parents' estrogen receptor α gene, or from the polymorphisms in his own estrogen receptor α gene, the development of the multifactorial disease in the boy can be prevented by means of providing his mother medical guidance, administering an inhibitor to endocrine disruptors, and the like.

Further, even when cryptorchidism has developed in a boy, since it is not a disease resulting from abnormalities in the patient's endocrine system, future fecundity is highly likely to be maintained by performing an early operation. In particular, in cases involving hypoplasia of the gubernaculum testis, it is expected that fecundity is highly likely to be maintained by an early operation.

Likewise, when a girl/women carrying similar polymorphisms to those described above has a multifactorial disease (for example, premature thelarche, precocious puberty, and endometriosis) ascribed to endocrine disruptors, her susceptibility to endocrine disruptors is likely to have increased. Preventive measures against such diseases can conceivably be taken by means of providing her mother medical guidance, administering an inhibitor to endocrine disruptors, and the like, as is the case with a boy.

EXAMPLES

Hereinafter, the present invention will be explained in more detail with reference to Examples and Drawings.

Example 1

Extraction of DNA and Determination of Nucleotides at SNPs

Genomic DNA was extracted from peripheral leukocytes and the SNPs were genotyped by TaqMan method.

For determining sequences containing SNPs 11, 14, and 15, the primers used for PCR by TaqMan method are as follows:

```
<SNP11>
SNP11S:     GTTTGGTCACTAGAAGTGGAG    (SEQ ID NO: 8)

SNP11A:     AAGGGTGTCCCAAGACCCAC     (SEQ ID NO: 9)

<SNP14>
SNP14S:     TCTCAGGAGCGTGTGGAACC     (SEQ ID NO: 10)

SNP14A:     TTGCTGGGTCTCTGCAGCAC     (SEQ ID NO: 11)

<SNP15>
SNP15S:     AGGAGACGGACCAAAGCCAC     (SEQ ID NO: 12)

SNP15A:     GCCATTGGTGTTGGATGCATGC   (SEQ ID NO: 13)
```

The other SNPs (SNPs 8 to 10, 12 and 13) were detected using Assays-on-Demand™ SNP Genotyping Products (Applied Biosystems). (ABI ID Numbers are 328969, 11410643, 8790212, 2823640, and 2823662, respectively).

Example 2

Statistical Analysis of SNPs in Multifactorial Diseases

DNAs were extracted from 100 normal individuals, 70 micropenis patients, 63 cryptorchidism patients, and the nucleotides at SNPs 1 to 15 in the estrogen receptor gene were determined. Table 1 shows an example of the data from the normal individuals.

TABLE 1

| SNP | 1  | 2  | 3  | 4  | 5  | 6  | 7  | 8  | 9  | 10 | 11 | 12 | 13 | 14 | 15 |
|-----|----|----|----|----|----|----|----|----|----|----|----|----|----|----|----|
| A01 | GG | AG | TT | GT | CG | GC | CT | AG | GG | AG | AG | GG | CC | CC | GG |
| A02 | GA | AA | TT | GT | CC | CC | CC | AA | AG | AG | AG | AG | CT | AA | GG |
| A03 | GG | AG | TT | GT | CG | GC | CC | GG | GG | GG | AA | GG | CC | CC | GG |
| A04 | GG | AG | CT | TT | CC | CC | TT | GG | GG | GG | AA | GG | CC | CC | AG |
| A05 | GG | AG | TT | GT | CG | CC | CC | AA | GG | GG | GG | GG | TT | AA | AG |
| A06 | GG | GG | CT | GT | CC | CC | CT | AG | GG | AG | AG | AG | CT | AC | GG |
| A08 | GG | AG | CT | GT | CC | CC | CT | AG | GG | GG | AG | GG | CT | AC | GG |
| A09 | GA | AG | CT | TT | CC | CC | TT | GG | GG | AG | AG | AG | CT | AC | AG |
| A10 | GA | AG | CT | GT | CC | CC | TT | GG | GG | AG | AG | AG | CT | AC | GG |

TABLE 1-continued

| SNP | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| A11 | GA | AG | TT | GG | GG | CC | TT | GG | GG | GG | AA | GG | CC | CC | GG |
| A12 | GA | AG | TT | TT | CC | GC | CT | GG | GG | GG | AA | GG | CC | CC | GG |
| A13 | GG | AG | CT | TT | CG | GC | CT | AG | AG | GG | AA | GG | CC | AC | GG |
| A15 | GG | AG | CT | GG | GG | GG | CC | AA | AA | AA | GG | AA | TT | AA | GG |
| A16 | GA | GG | TT | GG | GG | CC | TT | GG | GG | GG | AA | GG | CC | CC | AG |
| A17 | GG | GG | TT | TT | CC | CC | CC | GG | GG | GG | AA | GG | CC | CC | GG |
| A19 | GA | GG | TT | GT | CG | CC | CT | AG | AG | AG | AG | AG | CT | AC | GG |
| A20 | GA | AA | CT | GT | CG | CC | TT | GG | GG | GG | AA | GG | CC | AA | GG |
| A22 | GG | AG | CT | GG | CG | GC | CC | AA | AG | AA | GG | AG | TT | AA | GG |
| A24 | GG | GG | TT | GT | CG | CC | CT | AG | AG | AG | AG | AG | CT | AC | AA |
| A26 | GG | AG | TT | GG | GG | GC | CT | AG | AG | AG | AG | AG | CT | AC | GG |
| A28 | GA | AG | TT | GT | CG | CC | CT | GG | GG | GG | AG | GG | CT | AC | GG |
| A30 | GG | GG | CT | GT | CG | CC | TT | GG | GG | GG | AA | GG | CC | AC | GG |
| A31 | GG | AG | TT | GG | CG | GC | CC | AG | GG | AG | AG | AG | CT | AC | GG |
| A32 | GG | AG | CT | TT | CC | CC | CT | AG | GG | AG | AA | AG | TT | AA | GG |
| A33 | GG | AG | CT | GT | CC | GC | CT | AG | AG | AG | AG | AG | CT | AC | GG |
| A34 | GG | AG | TT | GT | CG | GC | CC | AA | AG | AG | GG | AG | TT | CC | AG |
| A35 | GG | AG | TT | TT | CG | CC | CT | AG | GG | GG | AG | GG | CT | AC | GG |
| A36 | GA | AG | TT | GT | CC | CC | CT | GG | GG | GG | AA | GG | CC | AC | GG |
| A37 | GG | GG | TT | GG | GG | GG | CC | AG | AG | AG | AG | AG | CT | AC | GG |
| A39 | GA | AG | CT | TT | CG | GC | CT | AG | GG | GG | AG | GG | CT | AC | GG |
| A40 | GA | AA | CT | GG | GG | GC | CT | AG | AG | AG | AG | AG | CT | AC | AG |
| A41 | GA | AG | TT | GT | GG | GC | CT | AG | GG | AG | GG | GG | CT | AC | AG |
| A43 | GA | AA | CT | TT | CC | CC | TT | GG | GG | GG | AA | GG | CC | CC | AG |
| A45 | GG | GG | TT | GG | GG | GG | CC | AG | AG | AG | AG | AG | CT | AC | GG |
| A46 | AA | AG | CT | TT | CG | CC | TT | GG | GG | GG | AA | GG | CC | CC | AG |
| A47 | GG | GG | TT | GG | CG | GC | CC | AG | GG | GG | AG | GG | CT | AC | GG |
| A49 | GA | AG | TT | GG | GG | GC | TT | GG | GG | GG | AA | GG | CC | CC | AG |
| A50 | GA | AA | CT | GT | CC | CC | CT | AA | AG | AA | GG | AG | TT | AA | GG |
| A51 | GG | AG | TT | GG | GG | GG | CC | AA | AA | AA | GG | AA | TT | AA | AG |
| MC 175 | GG | GG | TT | GG | CG | GC | CC | AA | AG | AA | GG | AG | TT | AA | AG |
| MC 176 | GA | AG | TT | GG | GG | GG | CC | AG | GG | AG | AG | GG | CT | AC | GG |
| MC 177 | GG | GG | CT | GG | CG | GC | CC | AG | AG | AG | AG | AG | CT | AC | GG |
| MC 178 | GA | AG | CT | GT | CG | GC | CT | AG | AG | AG | AG | AG | CT | AC | GG |
| MC 179 | GG | GG | TT | GG | GG | GC | CC | AA | GG | GG | GG | GG | CC | CC | AG |
| MC 180 | GG | AG | CT | GT | CC | GC | CC | AG | AG | AG | AG | AG | TT | AC | AG |
| MC 181 | GG | AG | TT | GT | CC | CC | CC | AA | AG | GG | GG | GG | TT | AA | GG |
| MC 182 | GA | AA | CT | TT | CC | CC | CT | AG | GG | GG | AA | GG | CC | AC | AG |

TABLE 1-continued

| SNP | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| MC 183 | GA | GG | TT | GG | CG | GC | CC | AA | AG | GG | AG | GG | CT | AC | AG |
| MC 184 | GG | AG | TT | GG | CC | CC | CT | GG | GG | GG | AA | GG | CC | CC | GG |
| MC 185 | GG | AG | CC | TT | CC | CC | CT | AG | GG | GG | AG | GG | CT | AC | AG |

Based on the results obtained, the chi-square test was conducted to examine, for each of the SNPs, whether there is any deviation in the nucleotide at the SNP between the normal individuals and the micropenis patients as well as between the normal individuals and the cryptorchidism patients. The results are shown in Table 2.

TABLE 2

| SNP | Polymorphism (wild-type/mutated) | Significant difference in occurrence frequency of polymorphisms (p) | | |
|---|---|---|---|---|
| | | Normal vs CO | Normal vs MP | Normal vs CO + MP |
| 1 | A/G | 0.3 | 0.23 | 0.18 |
| 2 | G/A | 0.23 | 0.77 | 0.27 |
| 3 | T/C | 0.62 | 0.97 | 0.71 |
| 4 | G/T | 0.5 | 0.65 | 0.47 |
| 5 | C/G | 0.97 | 0.96 | 1 |
| 6 | C/G | 0.89 | 0.14 | 0.35 |
| 7 | C/T | 0.06 | 0.1 | 0.03 |
| 8 | G/A | 0.15 | 0.03 | 0.05 |
| 9 | G/A | 0.09 | 0.04 | 0.003 |
| 10 | G/A | 0.006 | 0.01 | 0.001 |
| 11 | A/G | 0.007 | 0.01 | 0.001 |
| 12 | G/A | 0.01 | 0.02 | 0.003 |
| 13 | C/T | 0.008 | 0.01 | 0.001 |
| 14 | C/A | 0.02 | 0.02 | 0.007 |
| 15 | G/A | 0.48 | 0.76 | 0.51 |

CO: cryptorchidism
MP: micropenis

For micropenis, a significant difference ($p<0.05$) was found at SNPs 8 to 14; and for cryptorchidism, a significant difference ($p<0.05$) was found at SNPs 10 to 14. It was therefore demonstrated that there are associations between the onset of micropenis and each of the high susceptibility alleles at SNPs 8 to 14, and between the onset of cryptorchidism and each of the high susceptibility alleles at SNPs 10 to 14.

Thus, SNPs in a human estrogen receptor gene can be used as diagnostic markers for evaluating susceptibility of a human individual to a multifactorial disease. Taken together, SNPs in a human estrogen receptor gene are useful as diagnostic markers for evaluating susceptibility of a human individual to a multifactorial disease.

Example 3

Statistical Analysis of SNPs in Severe and Mild Micropenis

DNAs were extracted from 47 normal individuals and 33 or 37 patients with mild or severe micropenis, and the nucleotides at SNPs 1 to 15 in the estrogen receptor α gene were determined. Extraction of DNA and determination of nucleotide sequences containing SNPs were performed using the methods described in Example 1. Examples of data from the mild and severe micropenis patients are shown in Tables 3 and 4, respectively. Examples of data from total micropenis patients (a sum of the mild and severe micropenis patients) are shown in Table 5.

TABLE 3

| Case | SNP8 | SNP9 | SNP10 | SNP11 | SNP12 | SNP13 | SNP14 | SNP15 |
|---|---|---|---|---|---|---|---|---|
| 1 | AA | AG | AG | GG | AG | TT | AA | GG |
| 2 | AG | GG | AG | AG | GG | CT | AC | GG |
| 3 | GG | GG | GG | AA | GG | CC | CC | GG |
| 4 | AA | AA | AA | GG | AA | TT | AA | GG |
| 5 | GG | GG | AG | AG | AG | CT | AC | GG |
| 6 | GG | GG | GG | AA | GG | CC | CC | GG |
| 7 | AG | AG | AG | AG | AG | CT | AC | GG |
| 8 | AA | AG | GG | GG | GG | CT | AC | AG |
| 9 | AG | GG | AG | AG | GG | CT | AC | GG |
| 10 | AA | AG | AA | GG | AG | TT | AA | GG |
| 11 | GG | GG | AG | AG | GG | CT | AC | AG |
| 12 | GG | GG | AG | AA | GG | CC | CC | GG |
| 13 | AG | GG | AG | AG | GG | CT | AC | GG |
| 14 | GG | GG | AG | AG | AG | CT | AC | AA |
| 15 | AG | GG | AG | AG | GG | CT | AC | GG |
| 16 | GG | GG | GG | AA | GG | CC | CC | GG |
| 17 | AA | GG | GG | GG | GG | CT | AC | GG |
| 18 | GG | GG | AG | AG | AG | CT | AC | AG |
| 19 | AG | AG | AG | AG | AG | CT | AC | AG |
| 20 | AG | GG | GG | AG | GG | CC | CC | AG |
| 21 | GG | GG | GG | AA | GG | CC | CC | GG |
| 22 | AG | GG | AG | AG | GG | CT | AC | GG |
| 23 | AG | GG | AA | GG | AG | CT | AA | AG |
| 24 | GG | GG | GG | AA | GG | CC | CC | GG |
| 25 | AA | AA | AA | GG | AA | TT | AA | AG |
| 26 | AG | AG | AG | AG | GG | CT | AC | AG |
| 27 | AG | AG | AA | GG | AA | TT | AA | AG |
| 28 | AG | AG | AG | AG | AG | CT | CC | GG |
| 29 | GG | GG | GG | AA | GG | CC | CC | AG |
| 30 | AG | AG | GG | AA | GG | CC | CC | GG |
| 31 | AG | AG | AG | AG | AG | CT | AC | GG |

TABLE 3-continued

| Case | SNP8 | SNP9 | SNP 10 | SNP11 | SNP12 | SNP13 | SNP14 | SNP15 |
|---|---|---|---|---|---|---|---|---|
| 32 | AG | AG | AG | AG | AG | CT | AC | GG |
| 33 | AG | AG | AG | AG | AG | CT | AC | GG |

TABLE 4

| Case | SNP8 | SNP9 | SNP 10 | SNP11 | SNP12 | SNP13 | SNP14 | SNP15 |
|---|---|---|---|---|---|---|---|---|
| 1 | AG | GG | GG | AG | GG | CT | AC | GG |
| 2 | AA | AG | AG | GG | AG | TT | AA | AG |
| 3 | AA | AG | AG | GG | AG | TT | AA | GG |
| 4 | GG | GG | GG | AA | GG | CC | CC | GG |
| 5 | GG | GG | GG | AA | GG | CC | CC | GG |
| 6 | AA | AG | AG | AG | GG | CT | AC | GG |
| 7 | AG | AG | AA | GG | AA | TT | AA | GG |
| 8 | GG | GG | GG | AA | GG | CC | CC | AA |
| 9 | AG | AG | AG | AG | AG | CT | AC | AG |
| 10 | AG | AG | AA | GG | AA | TT | AA | AG |
| 11 | AG | GG | AG | AG | GG | CT | AC | GG |
| 12 | GG | AG | GG | AA | GG | CC | CC | GG |
| 13 | AG | AG | AG | AG | AG | CT | AC | AG |
| 14 | AG | GG | GG | AG | GG | CC | CC | GG |
| 15 | AA | AG | AG | GG | AG | TT | AA | GG |
| 16 | AA | AG | AG | GG | AG | TT | AA | GG |
| 17 | AA | AG | AG | GG | AG | TT | AA | GG |
| 18 | AA | AG | AA | GG | AG | TT | AA | GG |
| 19 | AG | AG | AG | AG | AG | CT | AC | AG |
| 20 | AA | AG | AA | GG | AA | TT | AA | GG |
| 21 | AG | GG | AG | AG | GG | CT | AC | GG |
| 22 | AG | AG | AG | AG | GG | CT | AC | AG |
| 23 | AA | AG | AG | GG | AG | TT | AA | AG |
| 24 | GG | AG | AG | AG | AG | CT | AC | GG |
| 25 | AA | AG | AA | GG | AG | TT | AA | GG |
| 26 | AA | AG | AG | AG | AG | CT | AC | GG |
| 27 | AG | GG | GG | AG | GG | CT | AC | GG |
| 28 | AG | GG | AG | AG | GG | CT | AC | GG |
| 29 | AA | AG | AG | AG | AG | CT | AC | AG |
| 30 | AA | AA | AA | GG | AA | TT | AA | AG |
| 31 | AG | GG | AG | AG | AG | CT | CC | AG |
| 32 | GG | GG | GG | AA | GG | CC | CC | GG |
| 33 | AG | GG | GG | AA | GG | CC | AC | AG |
| 34 | GG | GG | AG | AG | AG | CT | AC | GG |
| 35 | AA | AA | AG | AG | AG | CT | AC | GG |
| 36 | AG | GG | AG | GG | AG | TT | AA | GG |
| 37 | AG | GG | AG | GG | AG | TT | AA | GG |

TABLE 5

| Case | SNP8 | SNP9 | SNP 10 | SNP11 | SNP12 | SNP13 | SNP14 | SNP15 |
|---|---|---|---|---|---|---|---|---|
| 1 | AG | GG | GG | AG | GG | CT | AC | GG |
| 2 | AA | AG | AG | GG | AG | TT | AA | AG |
| 3 | AA | AG | AG | GG | AG | TT | AA | GG |
| 4 | GG | GG | GG | AA | GG | CC | CC | GG |
| 5 | GG | GG | GG | AA | GG | CC | CC | GG |
| 6 | AA | AG | AG | AG | GG | CT | AC | GG |
| 7 | AG | AG | AA | GG | AA | TT | AA | GG |
| 8 | GG | GG | GG | AA | GG | CC | CC | AA |
| 9 | AG | AG | AG | AG | AG | CT | AC | AG |
| 10 | AG | AG | AA | GG | AA | TT | AA | AG |
| 11 | AG | GG | AG | AG | GG | CT | AC | GG |
| 12 | GG | AG | GG | AA | GG | CC | CC | GG |
| 13 | GG | AG | AG | AG | AG | CT | AC | AG |
| 14 | AG | GG | GG | AG | GG | CC | CC | GG |
| 15 | AA | AG | AG | GG | AG | TT | AA | GG |
| 16 | AA | AG | AG | GG | AG | TT | AA | GG |
| 17 | AA | AG | AG | GG | AG | TT | AA | GG |
| 18 | AA | AG | AA | GG | AG | TT | AA | GG |
| 19 | AG | AG | AG | AG | AG | CT | AC | AG |
| 20 | AA | AG | AA | GG | AA | TT | AA | GG |
| 21 | AG | GG | AG | AG | GG | CT | AC | GG |
| 22 | AG | AG | AG | AG | GG | CT | AC | AG |
| 23 | AA | AG | AG | GG | AG | TT | AA | AG |
| 24 | GG | AG | AG | AG | AG | CT | AC | GG |
| 25 | AA | AG | AA | GG | AG | TT | AA | GG |
| 26 | AA | AG | AG | AG | AG | CT | AC | GG |
| 27 | AG | GG | GG | AG | GG | CT | AC | GG |
| 28 | AG | GG | AG | AG | GG | CT | AC | GG |
| 29 | AA | AG | AG | GG | AG | CT | AC | AG |

TABLE 5-continued

| Case | SNP8 | SNP9 | SNP 10 | SNP11 | SNP12 | SNP13 | SNP14 | SNP15 |
|---|---|---|---|---|---|---|---|---|
| 30 | AA | AA | AA | GG | AA | TT | AA | AG |
| 31 | AG | GG | AG | AG | AG | CT | CC | AG |
| 32 | GG | GG | GG | AA | GG | CC | CC | GG |
| 33 | AG | GG | GG | AA | GG | CC | AC | AG |
| 34 | GG | GG | AG | AG | AG | CT | AC | GG |
| 35 | AA | AA | AG | AG | AG | CT | AC | GG |
| 36 | AG | GG | AG | GG | AG | TT | AA | GG |
| 37 | AG | GG | AG | GG | AG | TT | AA | GG |
| 38 | AA | AG | AG | GG | AG | TT | AA | GG |
| 39 | AG | GG | AG | AG | GG | CT | AC | GG |
| 40 | GG | GG | GG | AA | GG | CC | CC | GG |
| 41 | AA | AA | AA | GG | AA | TT | AA | GG |
| 42 | GG | GG | AG | AG | AG | CT | AC | GG |
| 43 | GG | GG | GG | AA | GG | CC | CC | GG |
| 44 | AG | AG | AG | AG | AG | CT | AC | GG |
| 45 | AA | AG | GG | GG | GG | CT | AC | AG |
| 46 | AG | GG | AG | AG | GG | CT | AC | GG |
| 47 | AA | AG | AA | GG | AG | TT | AA | GG |
| 48 | GG | GG | AG | AG | GG | CT | AC | AG |
| 49 | GG | GG | AG | AA | GG | CC | CC | GG |
| 50 | AG | GG | AG | AG | GG | CT | AC | GG |
| 51 | GG | GG | AG | AG | AG | CT | AC | AA |
| 52 | AG | GG | AG | AG | GG | CT | AC | GG |
| 53 | GG | GG | GG | AA | GG | CC | CC | GG |
| 54 | AA | GG | GG | GG | GG | CT | AC | GG |
| 55 | GG | GG | AG | AG | AG | CT | AC | AG |
| 56 | AG | AG | AG | AG | AG | CT | AC | AG |
| 57 | AG | GG | GG | AG | GG | CC | CC | AG |
| 58 | GG | GG | GG | AA | GG | CC | CC | GG |
| 59 | AG | GG | AG | AG | GG | CT | AC | GG |
| 60 | AG | GG | AA | GG | AG | CT | AA | AG |
| 61 | GG | GG | GG | AA | GG | CC | CC | GG |
| 62 | AA | AA | AA | GG | AA | TT | AA | AG |
| 63 | AG | AG | AG | AG | GG | CT | AC | AG |
| 64 | AG | AG | AA | GG | AA | TT | AA | AG |
| 65 | AG | AG | AG | AG | AG | CT | CC | GG |
| 66 | GG | GG | GG | AA | GG | CC | CC | AG |
| 67 | AG | AG | GG | AA | GG | CC | CC | GG |
| 68 | AG | AG | AG | AG | AG | CT | AC | GG |
| 69 | AG | AG | AG | AG | AG | CT | AC | GG |
| 70 | AG | AG | AG | AG | AG | CT | AC | GG |

Based on the results obtained, the chi-square test was conducted to examine, for each of the SNPs, whether there is any deviation in the nucleotide at the SNP between the normal individuals and the mild micropenis patients, between the normal individuals and the severe micropenis patients, and between the normal individuals and the total micropenis patients. The results are shown in Table 6.

TABLE 6

| SNP (NCBI No.) | Genotyping analysis | | | | Statistical analysis (P-value) | | | T-MP vs. C | | M-MP vs. C | | S-MP vs. C | |
|---|---|---|---|---|---|---|---|---|---|---|---|---|---|
| | | T-MP (n = 70) | M-MP (n = 33) | S-MP (n = 37) | C (n = 47) | Allele | Genotype | A-F | G-F | A-F | G-F | A-F | G-F |
| SNP 1 (rs9340799) | GG | 42 | 23 | 19 | 33 | G vs. A | GG vs. GA + AA | 0.23 | 0.26 | 0.50 | 0.96 | 0.17 | 0.08 |
| | GA | 23 | 6 | 17 | 12 | | GG vs. GA vs. AA | | 0.51 | | 0.36 | | 0.15 |
| | AA | 5 | 4 | 1 | 2 | | GA + GG vs. AA | | 0.52 | | 0.19 | | 0.70 |
| SNP 2 (rs1643821) | GG | 22 | 12 | 10 | 13 | G vs. A | GG vs. GA + AA | 0.99 | 0.66 | 0.97 | 0.41 | 0.98 | 0.95 |
| | GA | 32 | 12 | 20 | 25 | | GG vs. GA vs. AA | | 0.64 | | 0.33 | | 0.99 |
| | AA | 16 | 9 | 7 | 9 | | GA + GG vs. AA | | 0.63 | | 0.39 | | 0.98 |
| SNP 3 (rs11155819) | TT | 45 | 23 | 22 | 34 | T vs. C | TT vs. TC + CC | 0.61 | 0.36 | 0.90 | 0.80 | 0.47 | 0.21 |
| | TC | 24 | 9 | 15 | 11 | | TT vs. TC vs. CC | | 0.32 | | 0.90 | | 0.13 |
| | CC | 1 | 1 | 0 | 2 | | CC vs. TC + TT | | 0.34 | | 0.78 | | 0.20 |
| SNP 4 (rs48700062) | GG | 19 | 9 | 10 | 26 | G vs. T | GG vs. GT + TT | 0.03 | 0.002 | 0.02 | 0.01 | 0.15 | 0.009 |
| | GT | 40 | 16 | 24 | 14 | | GG vs. GT vs. TT | | 0.01 | | 0.05 | | 0.01 |
| | TT | 11 | 8 | 3 | 7 | | TT vs. GT + GG | | 0.90 | | 0.29 | | 0.34 |
| SNP 5 (rs1801132) | GG | 14 | 6 | 8 | 19 | G vs. C | GG vs. CG + CC | 0.24 | 0.02 | 0.20 | 0.03 | 0.47 | 0.07 |
| | CG | 37 | 17 | 20 | 13 | | GG vs. CG vs. CC | | 0.01 | | 0.05 | | 0.04 |
| | CC | 19 | 10 | 9 | 15 | | CC vs. CG + GG | | 0.58 | | 0.88 | | 0.44 |

TABLE 6-continued

| SNP | | Genotyping analysis | | | | | | Statistical analysis (P-value) | | | | | |
| --- | --- | --- | --- | --- | --- | --- | --- | --- | --- | --- | --- | --- | --- |
| | | T-MP | M-MP | S-MP | C | | | T-MP vs. C | | M-MP vs. C | | S-MP vs. C | |
| (NCBI No.) | | (n = 70) | (n = 33) | (n = 37) | (n = 47) | Allele | Genotype | A-F | G-F | A-F | G-F | A-F | G-F |
| SNP 6 | CC | 27 | 16 | 11 | 20 | C vs. G | CC vs. CG + GG | 0.88 | 0.67 | 0.48 | 0.60 | 0.39 | 0.23 |
| (rs1884052) | CG | 37 | 15 | 22 | 22 | | CC vs. CG vs. GG | | 0.80 | | 0.73 | | 0.05 |
| | GG | 6 | 2 | 4 | 5 | | GG vs. CG + CC | | 0.71 | | 0.48 | | 0.98 |
| SNP 7 | CC | 28 | 9 | 19 | 17 | C vs. T | CC vs. CT + TT | 0.57 | 0.68 | 0.70 | 0.40 | 0.19 | 0.16 |
| (rs3020328) | CT | 34 | 20 | 14 | 23 | | CC vs. CT vs. TT | | 0.83 | | 0.59 | | 0.38 |
| | TT | 8 | 4 | 4 | 7 | | TT vs. CT + CC | | 0.58 | | 0.72 | | 0.58 |
| SNP 8 | GG | 19 | 11 | 8 | 14 | G vs. A | GG vs. AG + AA | 0.22 | 0.76 | 0.99 | 0.74 | 0.05 | 0.40 |
| (rs6905370) | AG | 31 | 16 | 15 | 26 | | GG vs. AG vs. AA | | 0.22 | | 0.83 | | 0.06 |
| | AA | 20 | 6 | 14 | 7 | | AA vs. AG + GG | | 0.09 | | 0.69 | | 0.02 |
| SNP 9 | GG | 34 | 19 | 15 | 28 | G vs. A | GG vs. AG + AA | 0.15 | 0.24 | 0.54 | 0.86 | 0.07 | 0.08 |
| (rs13203975) | AG | 32 | 12 | 20 | 19 | | GG vs. AG vs. AA | | 0.17 | | 0.23 | | 0.09 |
| | AA | 4 | 2 | 2 | 0 | | AA vs. AG + GG | | 0.10 | | 0.09 | | 0.11 |
| SNP 10 | GG | 19 | 10 | 9 | 23 | G vs. A | GG vs. AG + AA | 0.04 | 0.02 | 0.13 | 0.10 | 0.04 | 0.02 |
| (rs926778) | AG | 40 | 18 | 22 | 19 | | GG vs. AG vs. AA | | 0.06 | | 0.25 | | 0.07 |
| | AA | 11 | 5 | 6 | 5 | | AA vs. AG + GG | | 0.43 | | 0.55 | | 0.45 |
| SNP 11 | AA | 14 | 8 | 6 | 15 | A vs. G | AA vs. AG + GG | 0.07 | 0.14 | 0.43 | 0.46 | 0.03 | 0.10 |
| (rs3020364) | AG | 34 | 17 | 17 | 23 | | AA vs. AG vs. GG | | 0.20 | | 0.72 | | 0.09 |
| | GG | 22 | 8 | 14 | 9 | | GG vs. AG + AA | | 0.14 | | 0.58 | | 0.06 |
| SNP 12 | GG | 32 | 18 | 14 | 27 | G vs. A | GG vs. AG + AA | 0.07 | 0.21 | 0.38 | 0.80 | 0.03 | 0.07 |
| (rs6932902) | AG | 31 | 12 | 19 | 20 | | GG vs. AG vs. AA | | 0.06 | | 0.11 | | 0.03 |
| | AA | 7 | 3 | 4 | 0 | | AA vs. AG + GG | | 0.03 | | 0.04 | | 0.02 |
| SNP 13 | CC | 16 | 9 | 7 | 17 | C vs. T | CC vs. CT + TT | 0.14 | 0.12 | 0.91 | 0.40 | 0.02 | 0.08 |
| (rs3020371) | CT | 36 | 20 | 16 | 21 | | CC vs. CT vs. TT | | 0.28 | | 0.36 | | 0.09 |
| | TT | 18 | 4 | 14 | 9 | | TT vs. CT + CC | | 0.41 | | 0.40 | | 0.06 |
| SNP 14 | CC | 17 | 10 | 7 | 16 | C vs. A | CC vs. CA + AA | 0.11 | 0.25 | 0.76 | 0.73 | 0.02 | 0.12 |
| (rs3020375) | CA | 33 | 17 | 16 | 23 | | CC vs. CA vs. AA | | 0.28 | | 0.94 | | 0.07 |
| | AA | 20 | 6 | 14 | 8 | | AA vs. CA + CC | | 0.15 | | 0.89 | | 0.03 |
| SNP 15 | GG | 47 | 22 | 25 | 35 | G vs. A | GG vs. AG + AA | 0.41 | 0.40 | 0.46 | 0.45 | 0.51 | 0.49 |
| (rs2228480) | AG | 21 | 10 | 11 | 11 | | GG vs. AG vs. AA | | 0.70 | | 0.75 | | 0.79 |
| | AA | 2 | 1 | 1 | 1 | | AA vs. AG + GG | | 0.81 | | 0.80 | | 0.86 |

SNP: single nucleotide polymorphism;
NCBI; National Center for Biotechnology Information;
T-MP: total patients with micropenis;
M-MP: patients with mild micropenis (−2.1~−2.5 SD);
S-MP: patients with severe micropenis (<2-2.5 SD);
C: control males;
A-F: allele frequency: and
G-F: genotype frequency.

For severe micropenis, a significant differences (P<0.05) were found at SNP 8 and SNPs 10 to 14 (no significant difference was found at SNP 9 because normal children were the subjects here, whereas adult male were the subjects in Table 1). Thus, associations between the onset of the severe micropenis and the high susceptibility alleles at SNPs 8 to 14 were demonstrated.

On the other hand, for mild micropenis, a significant difference (P<0.05) was found at SNP 4, but no association with other SNPs was found. Thus, the mild micropenis is considered to include many cases from causes other than estrogen, indicating that the mild micropenis is not a multifactorial disease caused by endocrine disruptors.

Example 4

Haplotype and Diplotype Analyses in Mild and Severe Micropenis

The haplotype block encompassing SNPs 10 to 14 was analyzed using DNAs from normal individuals, mild micropenis patients and severe micropenis patients. DNAs were extracted by the method described in Example 1. Haplotypes were inferred by the software program LDSUPPORT (Kitamura, et al., Ann Hum Genet 2004;75:190-203) using the maximum likelihood method.

The D' value, the indicator of strength of the linkage disequilibrium was estimated by the method of Terwilliger and Ott (Terwilliger JD, Ott J, 1994, Johns Hopkins University Press), and a haplotype block was determined by the method of Zhu et al. (Zhu X, et al., 2003, Genome Res 13: 173-181) using the software program developed by Kamatani et al. (Kamatani N, et al., 2004, Am J Hum Genet 75:190-203). Further, the association with the qualitative phenotype on the basis of the haplotype was tested by PENHAPLO (Ito T. et al. Genetics 2004;168:2339-2348) using the maximum likelihood method.

From this haplotype analysis, a haplotype block was identified for an approximately 50 kb region encompassing SNPs 10 to 14. Thus, using information on the five SNP loci constituting this haplotype block, haplotype inference was performed in groups of the mild micropenis patients, the control, and the severe micropenis patients. The results are shown in Table 7.

TABLE 7

| Estimated haplotype (SNPs 10-14) | | GAGCC | AGATA | GGGTA | AGGTA |
|---|---|---|---|---|---|
| <Frequency of estimated haplotype> | | | | | |
| T-MP (n = 70) | | 42.1% (59/140) | 28.6% (40/140) | 9.3% (13/140) | 10.7% (15/140) |
| M-MP (n = 33) | | 48.5% (32/66) | 22.7% (15/66) | 4.5% (3/66) | 12.1% (8/66) |
| S-MP (n = 37) | | 36.5% (27/74) | 33.8% (25/74) | 13.5% (10/74) | 9.5% (7/74) |
| C (n = 47) | | 52.1% (49/94) | 21.3% (20/94) | 9.6% (9/94) | 9.6% (9/94) |
| <Comparison of estimated haplotype frequency> | | | | | |
| T-MP vs. C | P-value | 0.13 | 0.21 | 0.94 | 0.78 |
| | OR (95% CI) | 0.67 (0.40-1.13) | 1.48 (0.80-2.74) | 0.97 (0.40-2.36) | 1.13 (0.47-2.71) |
| M-MP vs. C | P-value | 0.65 | 0.83 | 0.23 | 0.61 |
| | OR (95% CI) | 0.86 (0.46-1.62) | 1.09 (0.51-2.32) | 0.45 (0.12-1.73) | 1.30 (0.47-3.57) |
| S-MP vs. C | P-value | 0.043 | 0.069 | 0.42 | 0.98 |
| | OR (95% CI) | 0.53 (0.28-0.98) | 1.89 (0.95-3.76) | 1.48 (0.57-3.84) | 0.99 (0.35-2.79) |
| <Association of estimated haplotype with micropenis> | | | | | |
| T-MP vs. C | P-value (D model)* | 0.16 | 0.39 | 0.95 | 0.67 |
| | OR (D model)* | 0.55 | 1.39 | 0.97 | 1.22 |
| | P-value (R model)† | 0.11 | 0.021 | 1.00 | 1.00 |
| | OR (R model)† | 0.49 | N.D.‡ | N.D.‡ | N.D.‡ |
| M-MP vs. C | P-value (D model)* | 0.74 | 0.78 | 0.21 | 0.40 |
| | OR (D model)* | 0.84 | 0.88 | 0.43 | 1.58 |
| | P-value (R model)† | 0.39 | 0.057 | 1.00 | 1.00 |
| | OR (R model)† | 0.63 | N.D.‡ | N.D.‡ | N.D.‡ |
| S-MP vs. C | P-value (D model)* | 0.055 | 0.12 | 0.38 | 0.98 |
| | OR (D model)* | 0.40 | 1.98 | 1.56 | 0.99 |
| | P-value (R model)† | 0.071 | 0.024 | 1.00 | 1.00 |
| | OR (R model)† | 0.37 | N.D.‡ | N.D.‡ | N.D.‡ |
| <Frequency of homozygotes> | | | | | |
| T-MP | | 12/70 | 5/70 | 0/70 | 0/70 |
| M-MP | | 7/33 | 2/33 | 0/33 | 0/33 |
| S-MP | | 5/37 | 3/37 | 0/37 | 0/37 |
| C | | 14/47 | 0/47 | 0/47 | 0/47 |
| <Comparison of homozygote frequency> | | | | | |
| T-MP vs. C | P-value | 0.11 | 0.061 | N.D.‡ | N.D.‡ |
| | OR (95% CI) | 0.49 (0.20-1.18) | N.D.‡ | N.D.‡ | N.D.‡ |
| M-MP vs. C | P-value | 0.39 | 0.087 | N.D.‡ | N.D.‡ |
| | OR (95% CI) | 0.63 (0.22-1.80) | N.D.‡ | N.D.‡ | N.D.‡ |
| S-MP vs. C | P-value | 0.076 | 0.047 | N.D.‡ | N.D.‡ |
| | OR (95% CI) | 0.37 (0.12-1.14) | N.D.‡ | N.D.‡ | N.D.‡ |

SNP: single nucleotide polymorphism;
OR: odds ratio;
CI: confidence interval;
T-MP: total patienmts with micropenis;
M-MP: patients with mild micropenis (−2.1~−2.5 SD);
S-MP: patients with severe micropenis patienmts with (<2.5 SD);
C: control males;
D model: dominant model;
R model: recessive model; and
N.D.: not determined.
*Homozygotes plus heterozygotes vs. non-carriers for the examined haplotype.
†Homozygous vs. heterozygotes plus non-carriers for the examined haplotype.
‡Not determined because of the absence of a homozygote in the control males.

The haplotypes involving SNPs 10 to 14 were indicated as the list of alleles at each locus (the nucleotide A, T, C, or G). The GAGCC and AGATA haplotypes were detected at higher frequencies in the group of the severe micropenis patients than in the normal group (GAGCC: 36.5% in the severe micropenis patient group vs. 52.1% in the normal group, P<0.043, by comparison of the haplotype frequency; AGATA: 33.8% in the severe micropenis patient group vs. 21.6% in the normal group, P=0.069, by comparison of the haplotype frequency).

Next, diplotypes were analyzed. Individuals homozygotes for the AGATA haplotype were detected at a higher frequency in the severe micropenis patient group than in the normal group (8.1% in the severe micropenis patient group vs. 0% in the normal group, P=0.047).

Example 5

Statistical Analysis of SNPs in Hypospadias

DNAs were extracted from 82 normal individuals and 43 hypospadias patients, and the nucleotides at SNPs 8 to 15 in the estrogen receptor α gene were determined. Extraction of DNA and determination of nucleotide sequences containing the SNPs were performed using the methods described in Example 1.

Examples of data from the child normal individuals are shown in Table 8, examples of data from the micropenis patients are shown in Table 9, examples of data from the cryptorchidism patients are shown in Table 10, and examples of data from the hypospadias patients are shown in Table 11.

TABLE 8

| Case | snp8 | snp9 | snp10 | snp11 | snp12 | snp13 | snp14 | snp15 |
|---|---|---|---|---|---|---|---|---|
| 1 | GG | GG | GG | AA | GG | CC | CC | GG |
| 2 | AG | AG | GG | AA | GG | CC | AC | AG |
| 3 | AG | GG | AG | AG | AG | CT | AC | AG |
| 4 | AA | AG | AG | GG | AG | TT | AA | GG |
| 5 | AA | AG | AA | GG | AG | TT | AA | AG |
| 6 | AG | AG | AG | AG | AG | CT | AC | GG |
| 7 | AA | AG | AG | GG | AG | TT | AA | AA |
| 8 | GG | GG | GG | AA | GG | CC | CC | GG |
| 9 | AG | AG | GG | AA | GG | CC | CC | GG |
| 10 | AG | GG | GG | AG | GG | CT | AC | GG |
| 11 | GG | GG | GG | AA | GG | CC | CC | AG |
| 12 | AG | AG | AG | AG | AG | CT | AC | GG |
| 13 | AG | GG | GG | AG | GG | CC | CC | AG |
| 14 | AG | GG | GG | AG | GG | CT | AC | GG |
| 15 | GG | GG | GG | AA | GG | CC | CC | GG |
| 16 | GG | GG | GG | AA | GG | CC | CC | GG |
| 17 | AG | AG | AG | AG | AG | CT | AC | GG |
| 18 | AG | GG | AA | GG | AG | TT | AA | GG |
| 19 | AG | AG | AG | AG | AG | CT | AC | GG |
| 20 | AG | AG | AG | AG | AG | CT | AC | GG |
| 21 | AG | GG | AG | AG | GG | CT | AC | GG |
| 22 | AG | AG | AG | AG | AG | CT | AC | AG |
| 23 | AA | AG | AA | GG | AG | TT | AA | GG |
| 24 | GG | GG | AG | AG | AG | CT | AC | AG |
| 25 | AG | AG | AG | AG | AG | CT | AC | GG |
| 26 | AG | GG | AA | GG | AG | TT | AA | GG |
| 27 | GG | GG | GG | AA | GG | CC | CC | GG |
| 28 | GG | GG | GG | AA | GG | CC | CC | GG |
| 29 | AG | GG | AG | GG | GG | CT | AC | AG |
| 30 | GG | GG | GG | AA | GG | CC | CC | GG |
| 31 | AG | GG | AG | AG | GG | CT | AC | GG |
| 32 | GG | GG | GG | AA | GG | CC | CC | GG |
| 33 | AG | AG | AG | AG | AG | CT | AC | GG |
| 34 | GG | GG | GG | AA | GG | CC | CC | GG |
| 35 | AG | GG | GG | AG | GG | CT | AC | GG |
| 36 | AG | GG | GG | AG | GG | CT | AC | GG |
| 37 | AG | AG | AG | AG | AG | CT | AC | GG |
| 38 | AA | AG | AA | GG | AG | TT | AA | GG |
| 39 | GG | GG | GG | AA | GG | CC | CC | AG |
| 40 | AG | AG | AG | AG | AG | CT | AC | GG |
| 41 | GG | GG | GG | AA | GG | CC | CC | GG |
| 42 | AG | AG | AG | AG | AG | CT | AC | AG |
| 43 | AG | GG | GG | AG | GG | TT | AC | GG |
| 44 | AG | GG | GG | AG | GG | CC | CC | GG |
| 45 | AA | GG | AG | GG | GG | TT | AA | GG |
| 46 | GG | GG | GG | AA | GG | CC | CC | GG |
| 47 | AA | AG | GG | AG | GG | CT | AC | AG |
| 48 | AA | GG | AG | AG | GG | CT | AA | GG |
| 49 | AA | GG | AG | GG | GG | TT | AA | GG |
| 50 | AA | GG | AG | GG | GG | CT | AC | GG |
| 51 | AG | AG | AG | AG | AG | CT | AC | GG |
| 52 | GG | GG | GG | AA | GG | CC | CC | GG |
| 53 | GG | GG | GG | AA | GG | CC | CC | AG |
| 54 | GG | GG | GG | AA | GG | CC | CC | AG |
| 55 | AG | GG | GG | AG | GG | CT | AC | GG |
| 56 | AA | AG | AA | GG | AG | TT | AA | GG |
| 57 | AG | AG | AG | AG | AG | CT | AC | GG |
| 58 | AA | GG | GG | GG | GG | CT | AC | GG |
| 59 | AG | GG | AA | GG | AG | TT | AA | AG |
| 60 | AG | AG | AG | AG | AG | CT | AC | GG |
| 61 | AG | AG | AG | AG | AG | CT | AC | AA |
| 62 | AG | GG | AG | GG | AG | TT | AA | AG |
| 63 | AG | AG | AG | AG | AG | CT | AC | GG |
| 64 | AG | GG | GG | AA | GG | CC | AC | AG |
| 65 | GG | GG | GG | AA | GG | CC | CC | GG |
| 66 | AG | AG | AG | AG | AG | CT | AC | AG |
| 67 | GG | GG | GG | AA | GG | CC | CC | AG |
| 68 | AA | GG | AG | GG | GG | CT | AA | AA |
| 69 | GG | GG | AG | AG | AG | CT | AA | GG |
| 70 | GG | GG | GG | AA | GG | CC | CC | GG |
| 71 | AG | GG | GG | AA | GG | CC | AC | AG |
| 72 | AG | AG | AG | AG | AG | CT | AC | GG |
| 73 | GG | GG | AG | AG | AG | CT | AC | AG |
| 74 | AG | GG | GG | AG | GG | CT | AC | GG |
| 75 | AG | AG | AG | AG | AG | CT | AC | GG |
| 75 | AA | AA | AA | GG | AA | TT | AA | GG |

TABLE 8-continued

| Case | snp8 | snp9 | snp10 | snp11 | snp12 | snp13 | snp14 | snp15 |
|---|---|---|---|---|---|---|---|---|
| 77 | GG | GG | GG | AA | GG | CC | CC | GG |
| 78 | AA | AA | AA | GG | AA | TT | AA | AG |
| 79 | GG | GG | GG | AA | GG | CC | CC | GG |
| 80 | GG | GG | GG | AA | GG | CC | CC | GG |
| 81 | AG | AG | AG | AG | AG | CT | AC | GG |
| 82 | GG | GG | GG | AA | GG | CC | CC | GG |

TABLE 9

| Case | SNP8 | SNP9 | SNP10 | SNP11 | SNP12 | SNP13 | SNP14 | SNP15 |
|---|---|---|---|---|---|---|---|---|
| 1 | AG | GG | GG | AG | GG | CT | AC | GG |
| 2 | AA | AG | AG | GG | AG | TT | AA | AG |
| 3 | AA | AG | AG | GG | AG | TT | AA | GG |
| 4 | GG | GG | GG | AA | GG | CC | CC | GG |
| 5 | GG | GG | GG | AA | GG | CC | CC | GG |
| 6 | AA | AG | AG | AG | GG | CT | AC | GG |
| 7 | AG | AG | AA | GG | AA | TT | AA | GG |
| 8 | GG | GG | GG | AA | GG | CC | CC | AA |
| 9 | AG | AG | AG | AG | AG | CT | AC | AG |
| 10 | AG | AG | AA | GG | AA | TT | AA | AG |
| 11 | AG | AG | AG | AG | GG | CT | AC | GG |
| 12 | GG | AG | GG | AA | GG | CC | CC | GG |
| 13 | GG | AG | AG | AG | AG | CT | AC | AG |
| 14 | AG | GG | GG | AG | GG | CC | CC | GG |
| 15 | AA | AG | AG | GG | AG | TT | AA | GG |
| 16 | AA | AG | AG | GG | AG | TT | AA | GG |
| 17 | AA | AG | AG | GG | AG | TT | AA | GG |
| 18 | AA | AG | AA | GG | AG | TT | AA | GG |
| 19 | AG | AG | AG | AG | AG | CT | AC | AG |
| 20 | AA | AG | AA | GG | AA | TT | AA | GG |
| 21 | AG | GG | AG | AG | GG | CT | AC | GG |
| 22 | AG | AG | AG | AG | GG | CT | AC | AG |
| 23 | AA | AG | AG | GG | AG | TT | AA | AG |
| 24 | GG | AG | AG | AG | AG | CT | AC | GG |
| 25 | AA | AG | AA | GG | AG | TT | AA | GG |
| 26 | AA | AG | AG | AG | AG | CT | AC | GG |
| 27 | AG | GG | GG | AG | GG | CT | AC | GG |
| 28 | AG | GG | AG | AG | GG | CT | AC | GG |

TABLE 9-continued

| Case | SNP8 | SNP9 | SNP10 | SNP11 | SNP12 | SNP13 | SNP14 | SNP15 |
|---|---|---|---|---|---|---|---|---|
| 29 | AA | AG | AG | GG | AG | CT | AC | AG |
| 30 | AA | AA | AA | GG | AA | TT | AA | AG |
| 31 | AG | GG | AG | AG | AG | CT | CC | AG |
| 32 | GG | GG | GG | AA | GG | CC | CC | GG |
| 33 | AG | GG | GG | AA | GG | CC | AC | AG |
| 34 | GG | GG | AG | AG | AG | CT | AC | GG |
| 35 | AA | AA | AG | AG | AG | CT | AC | GG |
| 36 | AG | GG | AG | GG | AG | TT | AA | GG |
| 37 | AG | GG | AG | GG | AG | TT | AA | GG |
| 38 | AA | AG | AG | GG | AG | TT | AA | GG |
| 39 | AG | GG | AG | AG | GG | CT | AC | GG |
| 40 | GG | GG | GG | AA | GG | CC | CC | GG |
| 41 | AA | AA | AA | GG | AA | TT | AA | GG |
| 42 | GG | GG | AG | AG | AG | CT | AC | GG |
| 43 | GG | GG | GG | AA | GG | CC | CC | GG |
| 44 | AG | AG | AG | AG | AG | CT | AC | GG |
| 45 | AA | AG | GG | GG | GG | CT | AC | AG |
| 46 | AG | GG | AG | AG | GG | CT | AC | GG |
| 47 | AA | AG | AA | GG | AG | TT | AA | GG |
| 48 | GG | GG | AG | AG | GG | CT | AC | AG |
| 49 | GG | GG | AG | AA | GG | CC | CC | GG |
| 50 | AG | GG | AG | AG | GG | CT | AC | GG |
| 51 | GG | GG | AG | AG | AG | CT | AC | AA |
| 52 | AG | GG | AG | AG | GG | CT | AC | GG |
| 53 | GG | GG | GG | AA | GG | CC | CC | GG |
| 54 | AA | GG | GG | GG | GG | CT | AC | GG |
| 55 | GG | GG | AG | AG | AG | CT | AC | AG |
| 56 | AG | AG | AG | AG | AG | CT | AC | AG |
| 57 | AG | GG | GG | AG | GG | CC | CC | AG |
| 58 | GG | GG | GG | AA | GG | CC | CC | GG |
| 59 | AG | GG | AG | AG | GG | CT | AC | GG |
| 60 | AG | GG | AA | GG | AG | CT | AA | AG |
| 61 | GG | GG | GG | AA | GG | CC | CC | GG |
| 62 | AA | AA | AA | GG | AA | TT | AA | AG |
| 63 | AG | AG | AG | AG | GG | CT | AC | AG |
| 64 | AG | AG | AA | GG | AA | TT | AA | AG |
| 65 | AG | AG | AG | AG | AG | CT | CC | GG |
| 66 | GG | GG | GG | AA | GG | CC | CC | AG |

TABLE 9-continued

| Case | SNP8 | SNP9 | SNP10 | SNP11 | SNP12 | SNP13 | SNP14 | SNP15 |
|------|------|------|-------|-------|-------|-------|-------|-------|
| 67 | AG | AG | GG | AA | GG | CC | CC | GG |
| 68 | AG | AG | AG | AG | AG | CT | AC | GG |
| 69 | AG | AG | AG | AG | AG | CT | AC | GG |
| 70 | AG | AG | AG | AG | AG | CT | AC | GG |

TABLE 10

| CYO | SNP8 | SNP9 | SNP10 | SNP11 | SNP12 | SNP13 | SNP14 | SNP15 |
|-----|------|------|-------|-------|-------|-------|-------|-------|
| 2 | AA | AG | AG | GG | AG | TT | AA | GG |
| 3 | GG | AG | GG | GA | GG | CT | AC | AG |
| 4 | AA | AA | AA | GG | AA | TT | AA | AG |
| 5 | GG | AG | AG | GA | AG | CT | AC | AG |
| 6 | AG | AG | AG | GA | AG | CT | AC | GG |
| 7 | GG | GG | GG | AA | GG | CC | CC | GG |
| 8 | AG | GG | AG | GA | GG | CT | AC | GG |
| 9 | AG | GG | AG | GA | GG | CT | AC | GG |
| 10 | AA | AA | AA | GG | AA | TT | AA | AG |
| 11 | GG | GG | GG | AA | GG | CC | CC | GG |
| 12 | GG | GG | GG | AA | GG | CC | CC | AG |
| 13 | AG | AG | GG | GA | GG | CT | AC | GG |
| 14 | AG | GG | GG | GA | GG | CT | AC | GG |
| 15 | AG | AG | AG | GA | AG | CT | AC | AG |
| 16 | AA | GG | GG | GG | GG | TT | AA | GG |
| 17 | AG | AG | AG | GA | AG | CT | AC | GG |
| 18 | AG | GG | AA | GG | GG | TT | AA | AG |
| 19 | AG | GG | GG | GA | GG | CC | CC | AG |
| 20 | AG | AG | AA | GG | AA | TT | AA | GG |
| 21 | AG | GG | AG | GA | GG | CT | AC | AG |
| 22 | GG | AG | AG | GA | AG | CT | AC | AG |
| 23 | AA | AA | AA | GG | AG | TT | AA | GG |
| 24 | AG | AG | AA | GG | AA | TT | AA | GG |
| 25 | AA | AG | AA | GG | AA | TT | AA | GG |
| 26 | AG | AG | AG | GA | AG | CT | AC | AG |
| 27 | AG | GG | GG | GA | GG | CT | AC | GG |
| 28 | AG | AG | GG | AA | GG | CC | CC | GG |
| 29 | AG | GG | AG | GA | GG | CT | AC | GG |
| 30 | AA | AA | AA | GG | AA | TT | AA | AA |
| 31 | GG | GG | GG | AA | GG | CC | CC | GG |
| 32 | GG | GG | GG | AA | GG | CC | CC | GG |
| 33 | GG | AG | GG | AA | GG | CC | CC | GG |
| 34 | AA | GG | GG | GG | GG | TT | AA | AG |
| 35 | AG | GG | AG | GG | AG | TT | AA | AA |
| 36 | GG | GG | GG | AA | GG | CC | CC | GG |
| 37 | AG | AG | AG | GA | AG | CT | AC | GG |
| 38 | AA | AA | AA | GG | AA | TT | AA | GG |
| 40 | AG | GG | GG | GA | GG | CC | CC | GG |
| 41 | AA | AG | GG | GA | GG | CT | AC | GG |
| 42 | AA | AA | AA | GG | AA | TT | AA | GG |
| 43 | AG | AG | AG | GA | AG | CT | AC | AG |
| 44 | AG | GG | AG | GG | AG | CT | AC | AA |
| 45 | AG | AG | AG | GA | AG | CT | AC | GG |
| 46 | AA | AA | AA | GG | AA | TT | AA | GG |
| 47 | GG | GG | GG | AA | GG | CC | CC | GG |
| 48 | GG | GG | GG | GA | GG | CC | CC | GG |
| 49 | GG | GG | AG | GA | AG | CT | AC | AA |
| 50 | AG | AG | AG | GA | AG | CT | AC | AG |
| 51 | AG | AG | AG | GA | AG | CT | AC | GG |
| 52 | AG | AG | AG | GA | AG | CT | AC | GG |
| 53 | GG | GG | GG | AA | GG | CC | CC | GG |
| 54 | AG | GG | AG | GG | AG | TT | AA | AG |
| 55 | AA | AG | AA | GG | AG | TT | AA | GG |
| 56 | AA | AG | AA | GG | AG | TT | AA | GG |
| 57 | GG | GG | GG | AA | GG | CC | CC | AG |
| 58 | AA | AA | AA | GG | AA | TT | AA | GG |
| 59 | AG | AG | AG | GA | AG | TT | AC | GG |
| 70 | GG | AG | AG | GA | AG | CT | AC | GG |
| 71 | AA | GG | AG | GG | GG | TT | AA | GG |
| 72 | AA | AG | AG | GG | AG | TT | AA | GG |
| 80 | AG | AG | AG | GA | AG | CT | AC | GG |
| 81 | AG | GG | GG | AA | AG | CT | AC | GG |
| 84 | AA | AG | AA | GG | AG | TT | AA | GG |

TABLE 11

| Case | snp8 | snp9 | snp10 | snp11 | snp12 | snp13 | snp14 | snp15 |
|---|---|---|---|---|---|---|---|---|
| 1 | GG | GG | GG | AA | GG | CC | CC | GG |
| 2 | AG | AG | AA | GG | AA | TT | AA | GG |
| 3 | GG | AG | AG | GA | AG | CT | AC | AA |
| 4 | AG | AG | AG | GA | AG | CT | AC | GG |
| 5 | AA | AA | AA | GG | AA | TT | AA | GG |
| 6 | GG | GG | GG | AA | GG | CC | CC | GG |
| 7 | AG | GG | GG | GA | GG | CT | AC | GG |
| 8 | GG | AG | AG | GA | AG | CT | AC | GG |
| 9 | AG | AG | AG | GA | AG | CT | AC | AG |
| 10 | AA | AA | AA | GG | AA | TT | AA | AG |
| 11 | AG | AG | AG | GA | AG | CT | AC | GG |
| 14 | AG | AG | AG | GA | AG | CT | AC | GG |
| 16 | AG | GG | GG | GA | GG | CC | CC | AG |
| 18 | AG | GG | AG | GG | AG | TT | AA | GG |
| 21 | AA | AA | AA | GG | AA | TT | AA | GG |
| 22 | AA | AA | AA | GG | AA | TT | AA | GG |
| 23 | GG | GG | GG | AA | GG | CC | CC | AA |
| 24 | AA | AG | AA | GG | AG | TT | AA | GG |
| 25 | AG | GG | GG | AA | GG | CC | CC | GG |
| 26 | AG | AG | AG | GA | AG | CT | AC | GG |
| 27 | AG | GG | AG | GA | GG | CC | CC | GG |
| 28 | AA | AA | AA | GG | AA | TT | AA | GG |
| 29 | GG | GG | GG | AA | GG | CC | CC | GG |
| 30 | GG | GG | GG | AA | GG | CC | CC | AG |
| 31 | AG | GG | GG | GA | GG | CT | AC | GG |
| 32 | AA | AA | AA | GG | AA | TT | AA | AG |
| 33 | AG | AG | AG | GA | AG | CT | AC | GG |
| 34 | AA | AA | AA | GG | AA | TT | AA | GG |
| 35 | AG | AG | AG | GA | AG | CT | AC | AG |
| 36 | AA | AA | AA | GG | AA | TT | AA | GG |
| 37 | GG | GG | GG | AA | GG | CC | CC | GG |
| 38 | AG | AG | GG | AA | GG | CC | CC | GG |
| 39 | AG | GG | AG | GA | GG | CT | AC | AG |
| 40 | GG | GG | GG | AA | GG | CC | CC | GG |
| 41 | AG | AG | AA | GG | AA | TT | AA | AG |
| 42 | AG | GG | GG | GA | GG | CT | AC | GG |
| 43 | AG | GG | GG | GA | GG | CT | AC | GG |
| 44 | AA | AG | AG | GG | AG | CT | AC | AG |
| 45 | AG | GG | AG | GG | AG | TT | AA | GG |
| 46 | AA | AG | AA | GG | AG | TT | AA | GG |
| 47 | AG | GG | GG | GA | GG | CT | AC | GG |
| 48 | GG | GG | GG | AA | GG | CC | CC | GG |
| 49 | AA | AA | AA | GG | AA | TT | AA | AG |

Base on the results obtained, the chi-square test was conducted to examine, for each of the SNPs, whether there is any deviation in the nucleotide at the SNP between the normal individuals and the micropenis patients, between the normal individuals and the cryptorchidism patients, and between the normal individuals and the hypospadias patients. The results are shown in Table 12.

TABLE 12

| | Genotyping analysis | | | | | | Statistical analysis (P-value) | | | | | |
|---|---|---|---|---|---|---|---|---|---|---|---|---|
| SNP | | MP | CO | HS | CB | | | MP vs. CB | | CO vs. CB | | HS vs. CB | |
| (NCBI No.) | Genotype | (n = 70) | (n = 63) | (n = 43) | (n = 82) | Allele | Genotype | A-F | G-F | A-F | G-F | A-F | G-F |
| SNP 8 | GG | 19 | 16 | 10 | 26 | G vs. A | GG vs. AG + AA | 0.20 | 0.54 | 0.16 | 0.41 | 0.17 | 0.32 |
| (rs6905370) | AG | 31 | 29 | 21 | 41 | | GG vs. AG vs. AA | | 0.32 | | 0.32 | | 0.38 |
| | AA | 20 | 18 | 12 | 15 | | AA vs. AG + GG | | 0.13 | | 0.14 | | 0.21 |
| SNP 9 | GG | 34 | 28 | 19 | 52 | G vs. A | GG vs. AG + AA | 0.064 | 0.066 | 0.0048 | 0.023 | 0.0012 | 0.039 |
| (rs13203975) | AG | 32 | 27 | 15 | 28 | | GG vs. AG vs. AA | | 0.15 | | 0.014 | | 0.0017 |
| | AA | 4 | 8 | 9 | 2 | | AA vs. AG + GG | | 0.30 | | 0.016 | | 0.00053 |
| SNP 10 | GG | 19 | 22 | 16 | 38 | G vs. A | GG vs. AG + AA | 0.032 | 0.015 | 0.035 | 0.17 | 0.027 | 0.33 |
| (rs926779) | AG | 40 | 26 | 14 | 35 | | GG vs. AG vs. AA | | 0.051 | | 0.10 | | 0.027 |
| | AA | 11 | 15 | 13 | 9 | | AA vs. AG + GG | | 0.39 | | 0.039 | | 0.0072 |
| SNP 11 | AA | 14 | 12 | 10 | 27 | A vs. G | AA vs. AG + GG | 0.038 | 0.073 | 0.016 | 0.062 | 0.061 | 0.26 |
| (rs3020364) | AG | 33 | 28 | 17 | 37 | | AA vs. AG vs. GG | | 0.13 | | 0.073 | | 0.17 |
| | GG | 23 | 23 | 16 | 18 | | GG vs. AG + AA | | 0.13 | | 0.054 | | 0.069 |
| SNP 12 | GG | 32 | 29 | 18 | 47 | G vs. A | GG vs. AG + AA | 0.061 | 0.15 | 0.020 | 0.18 | 0.0014 | 0.10 |
| (rs6932902) | AG | 31 | 24 | 14 | 33 | | GG vs. AG vs. AA | | 0.092 | | 0.013 | | 0.00029 |
| | AA | 7 | 10 | 11 | 2 | | AA vs. AG + GG | | 0.049 | | 0.0038 | | 0.000057 |

TABLE 12-continued

| | | Genotyping analysis | | | | | | Statistical analysis (P-value) | | | | | |
| | | | | | | | | MP vs. CB | | CO vs. CB | | HS vs. CB | |
| SNP | | MP | CO | HS | CB | | | | | | | | |
| (NCBI No.) | Genotype | (n = 70) | (n = 63) | (n = 43) | (n = 82) | Allele | Genotype | A-F | G-F | A-F | G-F | A-F | G-F |
|---|---|---|---|---|---|---|---|---|---|---|---|---|---|
| SNP 13 | CC | 16 | 14 | 12 | 29 | C vs. T | CC vs. CT + TT | 0.063 | 0.092 | 0.0081 | 0.086 | 0.070 | 0.40 |
| (rs3020371) | CT | 35 | 26 | 16 | 38 | | CC vs. CT vs. TT | | 0.18 | | 0.033 | | 0.12 |
| | TT | 19 | 23 | 15 | 15 | | TT vs. CT + CC | | 0.19 | | 0.013 | | 0.039 |
| SNP 14 | CC | 17 | 14 | 12 | 26 | C vs. A | CC vs. CA + AA | 0.18 | 0.31 | 0.046 | 0.21 | 0.18 | 0.66 |
| (rs3020375) | CA | 33 | 27 | 16 | 39 | | CC vs. CA vs. AA | | 0.43 | | 0.14 | | 0.22 |
| | AA | 20 | 22 | 15 | 17 | | AA vs. CA + CC | | 0.26 | | 0.056 | | 0.085 |
| SNP 15 | GG | 47 | 43 | 31 | 58 | G vs. A | GG vs. AG + AA | 0.75 | 0.63 | 0.57 | 0.75 | 0.97 | 0.87 |
| (rs2228480) | AG | 21 | 16 | 10 | 21 | | GG vs. AG vs. AA | | 0.82 | | 0.75 | | 0.93 |
| | AA | 2 | 4 | 2 | 3 | | AA vs. AG + GG | | 0.78 | | 0.45 | | 0.79 |

SNPs 8-15 corresponds to those shown in FIG. 1 and FIG. 2.
SNP: single nucleotide polymorphism;
NCBI: National Center for Biotechnology Information;
MP: patients with micropenis;
CO: patients with cryptorchidism;
HS: patients with hypospadias;
CB: control boy subjects;
A-F: allele frequency; and
G-F: genotype frequency.
The odds ratios and the 95% confidence intervals are available on request.

For hypospadias, significant differences (P<0.05) were found at SNPs 9, 10, 12, and 13. Particularly, when the SNP 12 locus is homozygous A, a highly significant difference (P<0.0001) was observed. It was therefore demonstrated that there are associations between the onset of hypospadias and each of SNPs 9, 10, 12, and 13, and that there is particularly a strong association with SNP 12.

Example 6

Haplotype and Diplotype Analyses in Hypospadias

The haplotype block encompassing SNPs 10 to 14 was analyzed using DNAs from normal individuals and hypospadias patients. DNAs were extracted by the method described in Example 1. Haplotypes were inferred by the software program LDSUPPORT (Kitamura et al. Ann Hum Genet 2004; 75:190-203) using the maximum likelihood method. The D' values, the indicator of strength of linkage disequilibrium, were estimated by the method of Terwilliger and Ott (Terwilliger JD, Ott J, 1994, Johns Hopkins University Press), and a haplotype block was determined by method of Zhu et al. (Zhu X, et al., 2003, Genome Res 13: 173-181) using the software program developed by Kamataniet al. (KamataniN, et al., 2004, Am J Hum Genet 75:190-203) Further, the association with the qualitative phenotype on the basis of the haplotype was tested by PENHAPLO (Ito T. et al. Genetics 2004;168: 2339-2348).

From this haplotype analysis, a haplotype block was identified as an approximately 50 kb region encompassing SNPs 10 to 14. Thus, using information on the five SNP loci constituting this haplotype block, haplotype inference was performed in the hypospadias patient group and the control group. Similarly, haplotype inference was performed in micropenis and cryptorchidism. The results are shown in Table 13.

TABLE 13

| Estimated haplotype (SNPs 10-14) | | GAGCC | AGATA | GGGTA | AGGTA |
|---|---|---|---|---|---|
| | | <Frequency of estimated haplotype> | | | |
| MP (n = 70) | | 42.1% (59/140) | 30.0% (42/140) | 9.3% (13/140) | 10.7% (15/140) |
| CO (n = 63) | | 39.7% (50/126) | 34.0% (43/126) | 11.0% (14/126) | 10.3% (13/126) |
| HS (n = 43) | | 43.0% (37/86) | 41.9% (36/86) | 8.1% (7/86) | 3.5% (3/86) |
| CB (n = 82) | | 51.8% (85/164) | 22.6% (37/164) | 8.5% (14/164) | 9.8% (16/164) |
| Total (n = 391) | | 46.4% (363/782) | 28.8% (225/782) | 10.1% (79/782) | 8.1% (63/782) |
| | | <Comparison of estimated haplotype frequency> | | | |
| MP vs. CB | P-value | 0.11 | 0.14 | 0.84 | 0.85 |
| | OR (95% CI) | 0.68 (0.42-1.09) | 1.47 (0.88-2.46) | 1.10 (0.46-2.62) | 1.11 (0.49-2.50) |
| CO vs. CB | P-value | 0.044 | 0.034 | 0.55 | 1.00 |
| | OR (95% CI) | 0.61 (0.37-1.01) | 1.78 (1.02-3.09) | 1.34 (0.57-3.16) | 1.06 (0.45-2.47) |
| HS vs. CB | P-value | 0.23 | 0.0024 | 1.00 | 0.084 |
| | OR (95% CI) | 0.70 (0.40-1.23) | 2.46 (1.35-4.51) | 0.95 (0.31-2.64) | 0.34 (0.061-1.22) |
| | | <Assocation of estimated haplotype with phenotype> | | | |
| MP vs. CB | P-value (D model)[c] | 0.32 | 0.30 | 0.95 | 0.61 |
| | OR (D model)[c] | 0.70 | 1.41 | 1.03 | 1.24 |
| | P-value (R model)[d] | 0.077 | 0.051 | 1.00 | 1.00 |
| | OR (R model)[d] | 0.50 | 4.44 | 0.00 | 0.00 |

TABLE 13-continued

| Estimated haplotype (SNPs 10-14) | | GAGCC | AGATA | GGGTA | AGGTA |
|---|---|---|---|---|---|
| CO vs. CB | P-value (D model)[c] | 0.11 | 0.25 | 0.76 | 0.94 |
| | OR (D model)[c] | 0.56 | 1.48 | 1.14 | 0.97 |
| | P-value (R model)[d] | 0.096 | 0.0029 | 0.066 | 0.20 |
| | OR (R model)[d] | 0.51 | 7.55 | N.D.[e] | N.D.[e] |
| HS vs. CB | P-value (D model)[c] | 0.18 | 0.10 | 0.72 | 0.071 |
| | OR (D model)[c] | 0.58 | 1.87 | 0.84 | 0.32 |
| | P-value (R model)[d] | 0.47 | 0.000073 | 1.00 | 1.00 |
| | OR (R model)[e] | 0.73 | 13.75 | 0.00 | 0.00 |
| <Frequency of homozygotes> | | | | | |
| MP | | 17.1% (12/70) | 10.0% (7/70) | 0% (0/70) | 0% (0/70) |
| CO | | 17.5% (11/63) | 15.9% (10/63) | 3.2% (2/63) | 1.6% (1/63) |
| HS | | 25.6% (11/43) | 25.6% (11/43) | 0% (0/43) | 0% (0/43) |
| CB | | 29.3% (24/82) | 2.4% (2/82) | 0% (0/82) | 0% (0/82) |
| <Comparison of homozygote frequency> | | | | | |
| MP vs. CB | P-value | 0.080 | 0.049[f] | N.D.[g] | N.D.[g] |
| | OR (95% CI) | 0.50 (0.23-1.09) | 4.44 (0.89-22.14) | N.D.[h] | N.D.[h] |
| CO vs. CB | P-value | 0.10 | 0.0040 | 0.10 | 0.25 |
| | OR (95% CI) | 0.51 (0.23-1.14) | 7.55 (1.59-35.82) | N.D.[h] | N.D.[h] |
| HS vs. CB | P-value | 0.66 | 0.000057 | N.D.[g] | N.D.[g] |
| | OR (95% CI) | 0.83 (0.36-1.91) | 13.75 (2.89-65.53) | N.D.[h] | N.D.[h] |

SNP: single nucleotide polymorphism;
MP: patients with micropenis;
CO: patients with cryptorchidism;
HS: patients with hypospadias;
CB: control boy subjects;
OR: odds ratio;
CI: confidence interval;
D model: dominant model;
R model: recessive model: and
ND.: not determined.
[c]Homozygotes plus heterozygotes vs. non-carriers for the examined haplotype.
[d]Homozygotes vs. heterozygotes plus non-carriers for the examined haplotype.
[e]Not determined because the penetrance for individuals with this haplotype is estimated >1.0 in PENHAPLO algorithm.
[f]This P-value is unlikely to be significant, considering the multiple comparisons.
[g]Not determined because of the absence of a homozygote in both of the compared groups.
[h]Not determined because of the absence of homozygote in both or either of the compared groups.

The haplotypes involving SNPs 10 to 14 were indicated as the list of alleles at each locus (the nucleotide A, T, C, or G). The AGATA haplotype was detected at a higher frequency in the group of hypospadias patients group than in the normal group (41.9% in the hypospadias patient group vs. 22.6% in the normal group; P<0.005, odds ratio=2.46, as a result of a comparison of the haplotype frequency).

Next, diplotypes were analyzed. Homozygotes for the AGATA haplotype were detected at a higher frequency in the group of hypospadias patient group than in the normal group (25.6% in the hypospadias patient group vs. 2.4% in the normal group; P<0.0001, odds ratio=13.75).

Taken together, it was suggested that, in a human estrogen receptor α gene, homozygous SNPs at SNP10 (A/A), SNP 11 (G/G), SNP 12 (A/A), SNP 13 (T/T), and SNP 14 (A/A) are useful as diagnostic markers for evaluating susceptibility to hypospadias.

What is claimed is:

1. An isolated genomic DNA, comprising a part or a whole of a human estrogen receptor alpha (α) gene, the genomic DNA comprising a haplotype consisting of five of single nucleotide polymorphisms (SNPs) 10 to 14 at both alleles of the estrogen receptor α gene, the haplotype being AGATA.

2. A diagnostic marker for susceptibility to micropenis, cryptorchidism, or hyposopadias, comprising the isolated genomic DNA of claim 1.

* * * * *

UNITED STATES PATENT AND TRADEMARK OFFICE
CERTIFICATE OF CORRECTION

PATENT NO. : 7,601,828 B2
APPLICATION NO. : 11/434940
DATED : October 13, 2009
INVENTOR(S) : Tsutomu Ogata et al.

Page 1 of 1

It is certified that error appears in the above-identified patent and that said Letters Patent is hereby corrected as shown below:

Title Page (73) Assignee, add --Stagen Co., LTD. China (JP), Japan Health Sciences Foundation, Tokyo (JP)--.

Signed and Sealed this
Third Day of May, 2011

David J. Kappos
*Director of the United States Patent and Trademark Office*

```
SEQUENCE LISTING

<160>  13

<210>  1
<211>  210
<212>  DNA
<213>  Homo sapiens

<400>  1 aattttttct caaatgaatt cagttttttg ttttttttct taccactggt ttttactgca      60
tagcgtttgc ctgaagaaca ccactttgtt tcccaaggca agtagtcact acaaggcrag     120
ttttgttctg tctatcccaa ggcaaataga cagcagcaaa catagtgtgg agggctgctg     180
ggttcagtag aaaaccatca actatttcta                                       210
```

<210> 2
<211> 210
<212> DNA
<213> Homo sapiens

<400> 2
cggtgaagct tcagagaact ttattaggta tgtttactta acaaagagt gcattggggg    60 tgatgaagcc tagtcaaatt cacagaaagc taagrataac tttctgctag acattacctc   120
agaagaattc tattatttct aatacacaca cacacacaca cacacacaca cactcacact   180
ctctctctct ctctctctgt cattatgaat                                    210

<210> 3
<211> 210
<212> DNA
<213> Homo sapiens

<400> 3
tgggctacag tttcatctgc tttgtggaca gaagtgccac aaagagccga attgtcagtg    60
cagacccaca tgaatcatag atcttaacga rgttttact aacgactagc aaaggataca   120
agctaaaaat gggtacaagc aaacacagca tcattcatca ctgtaaagac tctgaactat   180
cacatggaac ttcaaaagga ttcttcttct                                    210

<210> 4
<211> 210
<212> DNA
<213> Homo sapiens

<400> 4
tctgcatttg aatgatcatt tgggagactc ttattgtcct atttgcactg aaaaagtcac    60
tgaatcatta ttttagaact ggaataacrc ctgagatcta ggccagcact ttgcaagttg   120
tgctctatgg gacttttcat ggaagtggct gaggagttgc cttgaaggaa ggcagaggga   180
gtgggtcttg ggacacccct ccagttataa                                    210

<210> 5
<211> 210
<212> DNA
<213> Homo sapiens

<400> 5
ccagggttca cttttcctca tgtcctcgcc gacaagcctg atattcttat ttgcctctta    60
gcgcttcagc cttttccctcr tgacttaacg gtgactccct tgagactact tgaaataata   120
agtttggatg gcaaggaaat acccttctgc tgtcacccct tgccataaga ctgagttact   180
ttgtaaacaa agaagattta cttggtcttc                                    210

<210> 6
<211> 210
<212> DNA
<213> Homo sapiens

<400> 6
gggtccagat cccacaatgg ctctttattg gatgagagtt ctgggagcag tgccactcag    60
ctacatggtg ccaggtcctg aacctgtgcc ttcttyggtg gagggctggc acgtgctgac   120
agctttcatg tgggcaatct gggaacttca gagaaggcag gcctattaag tgttaagact   180 ccccacccg aacttttact gagaaaaagt                                     210

```
<210>  7
<211>  210
<212>  DNA
<213>  Homo sapiens

<400>  7 caattgaatt tccactaaaa taaaatagct ctctagtata ttacaaaact acccattctg      60
caaactgcag gggagctact gatmatgctt ggaactgtgc caggcactgc ctgcataaaa     120
atgagtaagg tccacttcct ccatggactg ggttgggtag gaggcaaaga taattaacca    180
attattttaa tattatgagt tcagggttgt                                      210

<210>  8
<211>  21
<212>  DNA
<213>  Artificial Sequence
<220>
<223>  SNP11S

<400>  8 gtttggtcac tagaagtgga g                                                21

<210>  9
<211>  20
<212>  DNA
<213>  Artificial Sequence
<220>
<223>  SNP11A

<400>  9 aagggtgtcc caagacccac                                                  20

<210>  10
<211>  20
<212>  DNA
<213>  Artificial Sequence
<220>
<223>  SNP14S

<400>  10 tctcaggagc gtgtggaacc                                                  20

<210>  11
<211>  20
<212>  DNA
<213>  Artificial Sequence
<220>
<223>  SNP14A

<400>  11 ttgctgggtc tctgcagcac                                                  20

<210>  12
<211>  21
<212>  DNA
<213>  Artificial Sequence
<220>
<223>  SNP15S

<400>  12 gaggagacgg accaaagcca c                                                21
```

```
<210> 13
<211> 22
<212> DNA
<213> Artificial Sequence
<220>
<223> SNP15A

<400> 13
gccattggtg ttggatgcat gc                                              22
```